United States Patent [19]

Sauter et al.

[11] 4,414,225

[45] Nov. 8, 1983

[54] AZEPINE DERIVATIVES AND THEIR ANTI-THROMBOTIC COMPOSITIONS AND METHODS

[75] Inventors: Robert Sauter, Laupheim; Gerhart Griss, Biberach; Wolfgang Grell, Biberach; Rudolf Hurnaus, Biberach; Bernhard Eisele, Biberach; Walter Haarmann, Biberach; Eckhard Rupprecht, Aulendorf-Tannhausen, all of Fed. Rep. of Germany

[73] Assignee: Dr. Karl Thomae Gesellschaft mit beschränkter Haftung, Biberach an der Riss, Fed. Rep. of Germany

[21] Appl. No.: 348,496

[22] Filed: Feb. 12, 1982

[30] Foreign Application Priority Data

Feb. 18, 1981 [DE] Fed. Rep. of Germany ....... 3105858

[51] Int. Cl.$^3$ .................... A61K 31/40; C07D 495/04
[52] U.S. Cl. .................... 424/274; 424/275; 424/285; 548/453; 260/330.3; 260/330.9
[58] Field of Search ............... 548/453; 260/330.3, 260/330.9; 424/274, 275, 285

[56] References Cited

U.S. PATENT DOCUMENTS

| | | | |
|---|---|---|---|
| 3,758,501 | 9/1973 | Weiss et al. | 260/326.9 |
| 3,846,446 | 11/1974 | Weiss et al. | 260/326.9 |
| 3,849,441 | 11/1974 | Weiss et al. | 260/326.9 |

*Primary Examiner*—Henry R. Jiles
*Assistant Examiner*—Bernard Dentz
*Attorney, Agent, or Firm*—Hammond & Littell, Weissenberger & Muserlian

[57] ABSTRACT

Compounds of the formula

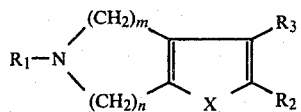

wherein
n and m are each 1, 2 or 3, and the sum of n+m is 4;
$R_1$ is alkyl; alkenyl; unsubstituted, mono- or di-substituted aralkyl; unsubstituted, mono- or di-substituted benzoyl; alkoxycarbonyl; aralkoxycarbonyl; or, when m and n are each 2 and/or $R_2$ and $R_3$ are other than both hydrogen at the same time, also hydrogen;
one of $R_2$ and $R_3$ is hydrogen or amino, and the other is carboxyl or alkoxycarbonyl; or, when $R_3$ is hydrogen,
$R_2$ is hydrogen; amino; alkoxycarbonyl-amino; (unsubstituted or mono-substituted phenyl)-aminocarbonyl-; (unsubstituted or mono-substituted phenyl)ethylaminocarbonyl; azidocarbonyl; or hydrazinocarbonyl;
X is oxygen, sulfur or

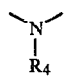

where $R_4$ is hydrogen; alkyl; phenyl-alkyl; or phenyl; non-toxic, pharmacologically acceptable acid addition salts thereof; and, when $R_2$ or $R_3$ is carboxyl, non-toxic, pharmacologically acceptable salts thereof formed with inorganic or organic bases. The compounds as well as their salts are useful as antithrombotics.

7 Claims, No Drawings

AZEPINE DERIVATIVES AND THEIR ANTI-THROMBOTIC COMPOSITIONS AND METHODS

This invention relates to novel azepine derivatives and non-toxic salts thereof, to methods of preparing these compounds, to pharmaceutical compositions containing them as active ingredients, and to methods of using them as antithrombotics.

More particularly, the present invention relates to a novel class of azepine derivatives represented by the formula

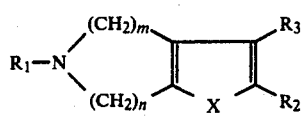

wherein n and m are each 1, 2 or 3, and the sum of n+m is 4;

$R_1$ is alkyl of 1 to 12 carbon atoms; alkenyl of 3 to 5 carbon atoms; unsubstituted, mono- or di-substituted aralkyl of 7 to 9 carbon atoms, where the substituents, which may be identical to or different from each other, are each hydroxyl or halogen; unsubstituted, mono- or di-substituted benzoyl, where the substituents, which may be identical to or different from each other, are each halogen or alkoxy of 1 to 3 carbon atoms; alkoxycarbonyl of 2 to 4 carbon atoms; aralkoxycarbonyl of 8 to 10 carbon atoms; or, when m and n are each 2 and/or $R_2$ and $R_3$ are other than both hydrogen at the same time, also hydrogen;

one of $R_2$ and $R_3$ is hydrogen or amino, and the other is carboxyl or alkoxycarbonyl of 2 to 4 carbon atoms; or, when $R_3$ is hydrogen, $R_2$ is hydrogen; amino; (alkoxycarbonyl of 2 to 6 carbon atoms) amino; (unsubstituted or mono-substituted phenyl)-aminocarbonyl, where the substituent is carboxyl or alkoxycarbonyl of 2 to 4 carbon atoms; (unsubstituted or mono-substituted phenyl)ethylaminocarbonyl, where the substituent is carboxyl or alkoxycarbonyl of 2 to 4 carbon atoms; azidocarbonyl; or hydrazinocarbonyl;

X is oxygen, sulfur or

where $R_4$ is hydrogen; alkyl of 1 to 3 carbon atoms; phenyl (alkyl of 1 to 3 carbon atoms); or phenyl; non-toxic, pharmacologically acceptable acid addition salts thereof; and, when $R_2$ or $R_3$ is carboxyl, non-toxic, pharmacologically acceptable salts thereof formed with inorganic or organic bases.

Examples of specific embodiments of substituents $R_1$, $R_2$, $R_3$ and X in formula I are the following:

$R_1$ is hydrogen, methyl, ethyl, propyl, isopropyl, butyl, isobutyl, pentyl, hexyl, heptyl, octyl, nonyl, decyl, undecyl, dodecyl, allyl, butenyl, pentenyl, benzyl, 1-phenylethyl, 1-phenylpropyl, 2-phenylethyl, 3-phenylpropyl, fluorobenzyl, chlorobenzyl, bromobenzyl, dichlorobenzyl, dibromobenzyl, hydroxychlorobenzyl, hydroxybromobenzyl, 2-(chlorophenyl)-ethyl, benzoyl, chlorobenzoyl, bromobenzoyl, fluorobenzoyl, dichlorobenzoyl, methoxybenzoyl, propoxybenzoyl, chloromethoxybenzoyl, bromoethoxybenzoyl, methoxycarbonyl, ethoxycarbonyl, propoxycarbonyl, isopropoxycarbonyl, benzyloxycarbonyl, 1-phenylethoxycarbonyl, 2-phenylethoxycarbonyl or 3-phenylpropoxycarbonyl;

One of $R_2$ and $R_3$ is hydrogen or amino and the other is carboxyl, methoxycarbonyl, ethoxycarbonyl, propoxycarbonyl or, when $R_3$ is hydrogen, $R_2$ is hydrogen, amino, methoxycarbonylamino, ethoxycarbonylamino, propoxycarbonylamino, isopropoxycarbonylamino, butoxycarbonylamino, tert-butoxycarbonylamino, azidocarbonyl, hydrazinocarbonyl, phenylaminocarbonyl, hydroxycarbonylphenylaminocarbonyl, methoxycarbonylphenylaminocarbonyl, ethoxycarbonylphenylaminocarbonyl, propoxycarbonylphenylaminocarbonyl, N-(2-phenylethyl)aminocarbonyl, N-[2-(4-carboxyphenyl)ethyl]-aminocarbonyl, N-[2-(4-methoxycarbonylphenyl)ethyl]aminocarbonyl, N-[2-(4-ethoxycarbonylphenyl)-ethyl]aminocarbonyl, N-[2-(4-propoxycarbonylphenyl)ethyl]-aminocarbonyl or N-[2-(4-isopropoxycarbonylphenyl)ethyl]-aminocarbonyl;

X is oxygen; sulfur atom, imino, methylimino, ethylimino, propylimino, isopropylimino, phenylimino, benzylimino, 1-phenylethylimino, 2-phenylethylimino, 1-phenylpropylimino or 3-phenylpropylimino.

A preferred subgenus is constituted by those compounds of the formula I where m is 1 or 2;

n is 2 or 3;

the sum of m+n is 4;

X is oxygen, sulfur, imino, methylimino, phenylimino or benzylimino;

$R_1$ is alkyl of 1 to 3 carbon atoms; unsubstituted mono- or di-substituted benzyl, where the substituents are chlorine or bromine; chlorohydroxybenzyl; bromohydroxybenzyl; unsubstituted or mono-substituted benzoyl, where the substituent is chlorine or bromine; alkoxycarbonyl of 2 to 4 carbon atoms; allyl; dodecyl; chloromethoxybenzoyl; benzyloxycarbonyl; or, when m and n are each 2 and/or $R_2$ and $R_3$ are other than both hydrogen at the same time, also hydrogen;

one of $R_2$ and $R_3$ is hydrogen or amino, and the other is alkoxycarbonyl of 2 to 4 carbon atoms; or, when $R_3$ is hydrogen, $R_2$ is hydrogen; amino; (alkoxycarbonyl of 2 to 5 carbon atoms)amino; N-phenyl-aminocarbonyl, where the phenyl moiety is mono-substituted in the 4-position by carboxyl or alkoxycarbonyl of 2 to 4 carbon atoms; N-(2-phenyl-ethyl)-aminocarbonyl, where the phenyl moiety is mono-substituted in the 4-position by carboxyl or alkoxycarbonyl of 2 to 4 carbon atoms; carboxyl; azidocarbonyl; or hydrazinocarbonyl;

non-toxic, pharmacologically acceptable acid addition salts thereof; and, when $R_2$ is carboxyl, non-toxic, pharmacologically acceptable salts thereof formed with inorganic or organic bases.

An especially preferred subgenus is constituted by those compounds of the formula I where m and n are each 2;

X is oxygen, sulfur, imino, methylimino, phenylimino or benzylimino;

$R_1$ is alkyl of 1 to 3 carbon atoms; unsubstituted mono- or di-substituted benzyl, where the substituents are chlorine or bromine; chlorohydroxybenzyl; bromohydroxybenzyl; unsubstituted or mono-substituted benzoyl, where the substituent is chlorine or bromine; alkoxycarbonyl of 2 to 4 carbon atoms; allyl; dodecyl; chloromethoxybenzoyl; or benzyloxycarbonyl;

$R_2$ is hydrogen, alkoxycarbonyl of 2 to 4 carbon atoms or carboxyl; and $R_3$ is hydrogen;

non-toxic, pharmacologically acceptable acid addition salts thereof; and, when $R_2$ is carboxyl, non-toxic, pharmacologically acceptable salts thereof formed with inorganic or organic bases.

A particularly preferred subgenus is constituted by compounds of the formula I where n and m are each 2, X is sulfur, $R_1$ is dodecyl, benzyl, chlorobenzyl or chlorobenzoyl, $R_2$ is hydrogen or carboxyl, and $R_3$ is hydrogen;

non-toxic, pharmacologically acceptable acid addition salts thereof; and, when $R_2$ or $R_3$ is carboxyl, non-toxic, pharmacologically acceptable salts thereof formed with inorganic or organic bases.

The compounds embraced by formula I may be prepared by the following methods:

Method A

By cyclizing a compound of the formula

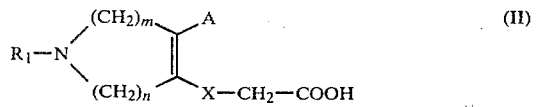

wherein m, n, X and $R_1$ have the same meanings as in formula I, and

A is cyano or formyl or their acetals, or an ester thereof, optionally formed in the reaction mixture, optionally followed by hydrolysis and/or decarboxylation.

The cyclization is advantageously carried out in a solvent such as methanol, ethanol, ether, dioxane, pyridine, triethylamine or mixtures thereof, in the presence of a base such as sodium carbonate, potassium hydroxide, sodium hydride, potassium tert. butoxide, morpholine or diethylamine or an aqueous base such as concentrated potassium hydroxide, at temperatures between 0° and 100° C., but preferably at temperatures between 0° C. and the boiling point of the reaction mixture.

The optional subsequent hydrolysis is advantageously carried out in a solvent such as water, ethanol, ethanol/water, dioxane or glacial acetic acid, in the presence of an acid such as hydrochloric, hydrobromic or sulfuric acid or in the presence of a base such as sodium hydroxide or potassium hydroxide, at temperatures between 60° and 120° C., but preferably at the boiling point of the reaction mixture.

The optional subsequent decarboxylation is preferably carried out in the presence of an acid such as hydrochloric, sulfuric, hydrobromic or phosphoric acid, which may simultaneously serve as a solvent, or with oxalic acid in a solvent such as water, ethanol/water, propanol, glacial acetic acid/water or dioxane/water at elevated temperatures, preferably at the boiling point of the reaction mixture, for instance at temperatures between 80° and 100° C.

A starting compound of the formula II is preferably prepared in the reaction mixture by reacting a corresponding haloazepine with a corresponding acetic acid derivative in a solvent such as pyridine, ethanol, ether or dioxane, and in the presence of a base such as triethylamine, sodium carbonate, sodium hydride, sodium methoxide or potassium tert. butoxide, at temperatures between 0° and 50° C.

Method B

By reacting an azepinone of the formula

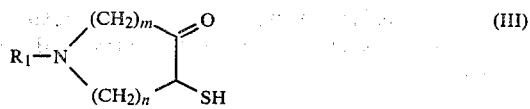

wherein m, n and $R_1$ have the same meanings as in formula I, optionally formed in the reaction mixture with a compound of the formula

$$NC-CH_2-COOH \qquad (IV)$$

or an ester thereof, optionally followed by hydrolysis and/or decarboxylation.

The reaction is advantageously carried out in a solvent such as methanol, ethanol or isopropanol, in the presence of a base such as sodium carbonate or pyridine or a secondary amine such as dimethylamine, diethylamine, piperidine or morpholine, where the organic bases may simultaneously serve as solvents, at temperatures between 0° and 100° C., but preferably at temperatures between 0° C. and the boiling point of the reaction mixture.

The optional subsequent hydrolysis is advantageously carried out in a solvent such as water, ethanol, ethanol/water, dioxane or glacial acetic acid, in the presence of an acid such as hydrochloric acid, hydrobromic acid or sulfuric acid or in the presence of a base such as sodium hydroxide or potassium hydroxide, at temperatures between 60° and 120° C., but preferably at the boiling point of the reaction mixture.

The optional subsequent decarboxylation is preferably carried out in the presence of an acid such as hydrochloric, sulfuric, hydrobromic or phosphoric acid, which may simultaneously serve as solvent, in a solvent such as water, ethanol/water, glacial acetic acid/water or dioxane/water, at elevated temperatures, preferably at the boiling point of the reaction mixture, for instance at temperatures between 80° and 100° C.

Method C

For the preparation of a compound of the formula I wherein at least one of $R_2$ and $R_3$ is hydrogen.

By decarboxylating a carboxylic acid of the formula

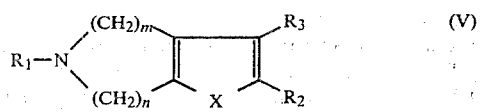

wherein m, n, X and $R_1$ have the same meanings as in formula I, and one of $R_2$ and $R_3$ is carboxyl and the other has the meanings previously defined for $R_2$ and $R_3$, optionally formed in the reaction mixture.

The decarboxylation is preferably carried out in the presence of an acid such as hydrochloric, sulfuric, hydrobromic or phosphoric acid, which may simultaneously serve as the solvent, or else with oxalic acid in a solvent such as water, ethanol/water, propanol, dimethylsulfoxide, glacial acetic acid/water or dioxane/water, at elevated temperatures, preferably at the boiling point of the reaction mixture, for instance at temperatures between 80° and 100° C.

Method D

For the preparation of a compound of the formula I wherein $R_1$ has the meanings previously defined with the exception of hydrogen.

By reacting a compound of the formula

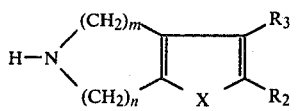

wherein $R_2$, $R_3$, m, n and X have the meanings previously defined, with a compound of the formula $$R_1\text{-}Z \qquad (VII)$$

wherein $R_1$ has the meaning previously defined with the exception of hydrogen, and Z is a nucleophilically exchangeable group, a hydroxyl group or, together with a hydrogen atom of the adjacent carbon atom, represents an oxygen atom.

The nucleophilically exchangeable group may, for example, be halogen such as chlorine, bromine or iodine, a sulfonyloxy group such as methanesulfonyloxy, methoxysulfonyloxy or p-toluenesulfonyloxy or additionally, in the case of acylation, a group of the formula —O—$COR_1$.

The reaction is advantageously carried out in a solvent such as ethanol, isopropanol, methylene chloride, chloroform, acetonitrile, toluene, dioxane, dimethylformamide or decalin, optionally in the presence of a base such as triethylamine, pyridine or sodium carbonate, in the presence of a hydrogenation catalyst such as Raney nickel or palladium-on-charcoal, or in the presence of a hydrogenation catalyst such as Raney nickel and under a hydrogen pressure of 1 to 10 bars at temperatures between 0° and 250° C., but preferably at temperatures between 20° and the boiling point of the solvent which is used.

When Z is a nucleophilically exchangeable group, the reaction is carried out with an alkylating agent such as ethyl iodide, benzyl chloride, dimethylsulfate or ethyl p-toluenesulfonate, or with an acylating agent such as ethyl chloroformate or 2-methoxy-5-chlorobenzoyl chloride, preferably in a solvent and in the presence of a base, at temperatures between 0° and 150° C., but preferably at temperatures between 20° and 80° C.

When Z is a hydroxyl group, the reaction is carried out with a corresponding alcohol such as methanol, ethanol, benzyl alcohol or o-chlorobenzyl alcohol, which may simultaneously act as the solvent, preferably in an atmosphere of nitrogen and in the presence of a hydrogenation catalyst, at temperatures between 80° and 250° C., but preferably at temperatures between 100° C. and the boiling point of the alcohol which is used.

When Z, together with a hydrogen atom of the adjacent carbon atom, represents an oxygen atom, the reaction is carried out in a solvent and in the presence of catalytically activated hydrogen at temperatures between 80° and 250° C., but preferably at temperatures between 100° and 200° C.

If, according to the invention, a compound of the formula I is obtained wherein $R_1$ is a benzyl group optionally mono- or di-substituted by hydroxyl groups and/or halogen atoms, and/or X is a benzylimino group, this compound may be converted by catalytic hydrogenation into a corresponding compound of the formula I wherein $R_1$ is hydrogen and/or X is an imino group, and/or a compound of the formula I wherein $R_1$ is a benzyl group optionally mono- or di-substituted by hydroxyl groups and/or halogen atoms may be converted, by means of Raney nickel in the presence of a corresponding alcohol, into a corresponding compound of the formula I wherein $R_1$ is alkyl of 1 to 12 carbon atoms. A compound of the formula I wherein $R_1$ and/or $R_2$ or $R_3$ are alkoxycarbonyl of 2 to 4 carbon atoms may be converted by hydrolysis with simultaneous decarboxylation, if $R_1$ is alkoxycarbonyl of 2 to 4 carbon atoms, into a corresponding compound of the formula I wherein $R_1$ is hydrogen and/or $R_2$ or $R_3$ is carboxyl.

A compound of the formula I wherein $R_2$ or $R_3$ is carboxyl may be converted by esterification or amidation into a corresponding compound of the formula I wherein $R_2$ or $R_3$ is alkoxycarbonyl of 2 to 4 carbon atoms or $R_2$ is N-phenyl-aminocarbonyl of N-phenylethyl-aminocarbonyl where the phenyl nucleus may be substituted by carboxyl or alkoxycarbonyl of 2 to 4 carbon atoms.

A compound of the formula I wherein $R_2$ is carboxyl of alkoxycarbonyl of 2 to 4 carbon atoms may be converted with hydrazine, optionally in the presence of an acid-activating agent or a dehydrating agent, into a corresponding compound of the formula I wherein $R_2$ is hydrazinocarbonyl.

A compound of the formula I wherein $R_2$ is carboxyl or hydrazinocarbonyl, may be converted by means of its acid halide or by means of a nitrite into a corresponding compound of the formula I wherein $R_2$ is azidocarbonyl.

A compound of the formula I wherein $R_2$ is azidocarbonyl may be converted with a corresponding alcohol into a corresponding compound of the formula I wherein $R_2$ is alkoxycarbonylamino of 2 to 6 carbon atoms. A compound of the formula I wherein $R_2$ is alkoxycarbonylamino of 2 to 6 carbon atoms may be converted by hydrolysis with simultaneous decarboxylation into a corresponding compound of the formula I wherein $R_2$ is amino.

The catalytic hydrogenation is preferably carried out in a solvent such as ethanol, ethyl acetate, glacial acetic acid or dioxane in the presence of a hydrogenation catalyst such as palladium or platinum and optionally in the presence of an acid such as 1 N hydrochloric acid under a hydrogen pressure of 2 to 10 bars and at a temperature between 20° and 100° C.

The reaction with a corresponding alcohol in the presence of Raney nickel is preferably carried out in the corresponding alcohol as the solvent at elevated temperatures, for instance at temperatures between 60° and 120° C.

The hydrolysis is advantageously carried out in a solvent such as water, ethanol, ethanol/water, dioxane or glacial acetic acid in the presence of an acid such as hydrochloric, hydrobromic or sulfuric acid or in the presence of a base such as sodium hydroxide or potassium hydroxide at temperatures between 60° and 120°

C., but preferably at the boiling point of the reaction mixture.

The esterification or amidation is advantageously carried out in a suitable solvent such as methanol, ethanol, chloroform, ether, dioxane, acetonitrile or dimethylformamide, optionally in the presence of an acid-activating agent or dehydrating agent, for instance in the presence of hydrogen chloride, sulfuric acid, thionyl chloride or N,N'-dicyclohexylcarbodiimide, and optionally in the presence of a base such as triethylamine or pyridine, at temperatures between 0° and 100° C., but preferably at temperatures between 20° C. and the boiling point of the reaction mixture. The esterification may also be carried out by trans-esterification, by alkylation of a corresponding carboxylic acid or a salt thereof with a corresponding alkyl halide or diazoalkane.

The hydrazide formation is advantageously carried out in a suitable solvent such as ethanol, dioxane, toluene or an excess of the hydrazine, optionally in the presence of an acid-activating agent or a dehydrating agent at temperatures between 20° and 120° C., but preferably at temperatures between 50° and 80° C.

The azide formation is preferably carried out in a solvent such as acetone, acetone/water, dioxane or water/dioxane at low temperatures, for instance at temperatures between −10° and 5° C. Starting from a compound of the formula I wherein $R_2$ is carboxyl, this compound is first converted with an acid-activating agent such as thionyl chloride into the corresponding reacting derivative, which is subsequently reacted with an alkali metal azide such as sodium azide to form the corresponding azide, or, starting from a compound of the formula I wherein $R_2$ is hydrazinocarbonyl, this compound is converted into the corresponding azide by means of a nitrite such as sodium nitrite in the presence of hydrochloric acid.

The conversion of an azidocarbonyl compound into a corresponding alkoxycarbonylamino compound in the presence of the corresponding alcohol is preferably carried out in a solvent such as dioxane at elevated temperatures, for instance at temperatures between 60° and 100° C.

Moreover, an isomer mixture of compounds of the formula I obtained according to the invention may subsequently be separated into the individual isomer components thereof by known methods, for example by chromatography on a solid carrier such as silica gel or by fractional crystallization.

The compounds of the formula I are basic and therefore form addition salts with inorganic or organic acids. Examples of non-toxic, pharmacologically acceptable acid addition salts are those formed with hydrochloric acid, hydrobromic acid, sulfuric acid, phosphoric acid, lactic acid, oxalic acid, citric acid, tartaric acid, succinic acid, maleic acid, fumaric acid or the like.

In addition, those compounds of the formula I wherein $R_2$ and/or $R_3$ are carboxyl form salts with inorganic or organic bases. Examples of non-toxic, pharmacologically acceptable such salts are those formed with sodium hydroxide, potassium hydroxide, cyclohexylamine or the like.

The starting compounds of the formulas II to VII are either described in the literature or may be obtained by methods described in the literature (see Examples A to O below). Thus, for example, a compound of the formula II is obtained by the Vilsmeier reaction with a corresponding azepinone. The chloroformyl compound thus obtained can then be converted, via the oxime, into the corresponding nitrile, which is then reacted with a corresponding acetic acid derivative to yield a compound of the formula II.

A starting compound of the formula III is obtained by reacting a corresponding haloazepinone with sodium hydrogen sulfide.

A starting compound of the formula V or VI is obtained by cyclization of a corresponding azepine derivative with a corresponding carboxylic acid derivative, and optional subsequent debenzylation.

The following examples illustrate the present invention and will enable others skilled in the art to understand it more completely. It should be understood, however, that the invention is not limited solely to the particular examples given below.

Preparation of Starting Compounds

Example A

1-Benzyl-4-chloro-5-formyl-2,3,6,7-tetrahydro-1H-azepine hydrochloride

The Vilsmeier complex prepared from 460 gm (3 mols) of phosphorus oxychloride and 292 gm (4 mols) of dimethylformamide was admixed at room temperature with 400 ml of methylene chloride and then with 240 gm (1 mol) of 1-benzylhexahydro-azepinone-(4)hydrochloride in two batches within one hour, while the temperature of the reaction mixture was maintained at about 20° C. The mixture was then stirred for 5 hours. After standing overnight it was poured over 1 kg of ice, and after being allowed to stand for 3 hours the methylene chloride phase was removed. The aqueous phase was extracted several times with chloroform. The combined organic extracts were dried over sodium sulfate and evaporated in a rotary evaporator. The semi-solid residue was triturated with 200 ml of isopropanol, suction-filtered off and washed with a little ice-cold isopropanol.

Yield: 85.3 gm (30% of theory),
Melting point: 215°–216° C.,
Calc.: C-58.76%; H-5.99%; N-4.90%; Cl-24.77%.
Found: C-58.60%; H-6.06%; N-4.81%; Cl-24.50%.

Example B

Ethyl 4-chloro-5-formyl-2,3,6,7-tetrahydro-1H-1-azepine carboxylate and

Ethyl 4-chloro-3-formyl-2,5,6,7-tetrahydro-1H-1-azepine carboxylate

The Vilsmeier complex prepared from 113.8 gm (1.5 mols) of dimethylformamide and 120 gm (0.78 mol) of phosphorus oxychloride, was admixed dropwise with 111 gm (0.6 mol) of ethyl hexahydroazepinone-(4)-1-carboxylate at 40° C. while stirring and the temperature of the reaction mixture was kept below 50° C. After the addition was complete, stirring was continued for 2 hours. Then, the mixture was stirred into 1.4 liters of ice-cold water, and the aqueous solution was extracted twice with ether. The combined ether extracts were washed twice with water and dried over sodium phosphate. After the solvent was distilled off in a rotary evaporator a yellow oil was left (1:1 mixture of the two isomers), which was further reacted without purification.

Yield: 93 gm (67% of theory).

Example C

Benzyl 4-chloro-5-formyl-2,3,6,7-tetrahydro-1H-1-azepine carbozylate and

Benzyl 4-chloro-3-formyl-2,5,6,7-tetrahydro-1H-1-azepine carboxylate

The Vilsmeier reagent prepared from 18.9 gm (0.26 mol) of dimethylformamide and 20 gm (0.13 mol) of phosphorus oxychloride was mixed at 40° to 45° C. with 24.3 gm (0.1 mol) of benzyl hexahydroazepinone-(4)-1-carboxylate, which was added dropwise, the temperature in the reaction mixture being kept below 50° C. After completion of the addition, stirring was continued for 2 hours. The mixture was then stirred into 250 ml of ice water, and the aqueous solution was extracted three times with ether. The combined ether extracts were washed twice with water and dried over sodium sulfate. After the solvent was distilled off, a yellowish oil was left (1:1 mixture of the two isomers), which was further reacted without being purified. Yield: 17.1 gm (60% of theory).

Example D

1-Benzyl 4-chloro-2,3,6,7-tetrahydro-5-oximinomethylene-1H-azepine hydrochloride 45 gm (0.16 mol) of 1-benzyl-4-chloro-5-formyl-2,3,6,7-tetrahydro-1H-azepine hydrochloride were suspended in 450 ml of ethyl alcohol, and at 30° C. 12.2 gm (0.175 mol) of hydroxylamine hydrochloride were added in batches while stirring. After some hours, a crystalline precipitate separated out of the gradually clearing solution. The reaction mixture was stirred for 2 hours more and then allowed to stand overnight. The crystalline precipitate was suction-filtered off and dried. After evaporation of the mother liquor, another 10 gm were obtained.

Total yield: 41.1 gm (86.8% of theory),
Melting point: 211° C.
Calc.: C-63.52%; H-6.47%; N-10.58%; Cl-13.39%.
Found: C-63.75%; H-6.58%; N-10.38%; Cl-13.30%.

Example E

1-Benzyl-4-chloro-5-cyano-2,3,6,7-tetrahydro-1H-azepine 43.5 gm (0.144 mol) of 1-benzyl-4-chloro-2,3,6,7-tetrahydro-5-oximinomethylene-1H-azepine hydrochloride were added to 450 ml of phosphorus oxychloride while stirring at ambient temperature. The mixture was then stirred for 3 hours more, and the reaction mixture was then allowed to stand overnight. Then, the excess phosphorus oxychloride was distilled off in a rotary evaporator, and the residue was carefully mixed with water while cooling with ice. While cooling was continued, the mixture was made slightly alkaline by the addition of concentrated ammonia, and an oil separated out which crystallized when scratched. The crystal slurry thus obtained was suction-filtered, washed with water, dried and recrystallized from isopropyl alcohol.

Yield: 31.6 gm (66.4% of theory),
Melting point: 50°-51° C.
Calc.: C-68.15%; H-6.13%; N-11.35%; Cl-14.37%.
Found: C-68.56%; H-6.09%; N-10.97%; Cl-14.22%.

Example F

1-Ethyl-4-chloro-2,3,6,7-tetrahydro-5-oximinomethylene-1H-azepine

The Vilsmeier reagent prepared from 31.98 gm (0.437 mol) of dimethylformamide and 51.15 gm (0.33 mol) of phosphorus oxychloride was mixed with 30 ml of methylene chloride and 14.78 gm (0.832 mol) of 1-ethyl-hexahydroazepinone-(4) hydrochloride, whereby the temperature rose to about 30° C. After stirring at room temperature for 1 hour, stirring was continued for 4 hours at 30° C. The reaction mixture was then poured over ice and made alkaline with soda, after being mixed with chloroform. After extracting 5 times with chloroform, the combined organic phases were acidified with ethereal hydrochloric acid and evaporated in a rotary evaporator. The dark oil thus obtained (16 gm $\triangleq$ 0.0714 mol) was dissolved in 150 ml of ethyl alcohol and stirred overnight at room temperature with 4.96 gm (0.714 mol) of hydroxylamine hydrochloride. The solvent was then distilled off in a rotary evaporator, the residue was mixed with water and, after mixing with chloroform, neutralized with sodium bicarbonate. The aqueous phase was evaporated to dryness in vacuo and extracted by boiling several times with chloroform. The combined chloroform phases were dried over sodium sulfate and evaporated in vacuo. The red oil obtained was filtered on a silicagel column (chloroform/ethyl alcohol 4:1).

After the solvent was distilled off from the corresponding fractions in vacuo, a reddish oil was obtained which solidified after scratching.

Yield: 7.7 gm (53.4% of theory),
Melting point: 90°-95° C.
Calc.: C-53.33%; H-7.46%; N-13.82%; Cl-17.49%.
Found: C-53.33%; H-7.36%; N-13.80%; Cl-17.68%.

Example G

Ethyl-4-chloro-5-formyl-2,3,6,7-tetrahydro-1H-1-azepine carboxylate

A solution of 3.6 gm (0.033 mol) of ethyl chloroformate in 15 ml of dry methylene chloride was added dropwise at room temperature, while stirring, within 30 minutes to a solution of 7.5 gm (0.03 mol) of 1-benzyl-4-chloro-5-formyl-2,3,6,7-tetrahydro-1H-azepine in 50 ml of dry methylene chloride, whereupon the temperature of the reaction mixture increased from 22° C. to 27° C. After the addition was complete, the mixture was stirred at room temperature for another 3 hours. Then, the methylene chloride was distilled off in a rotary evaporator, and the residue was distilled in a high vacuum.

Yield: 6.5 gm (93.8% of theory).
B.p.$_{0.26\ bar}$: 116°-118° C.
Calc.: C-51.84%; H-6.09%; N-6.05%; Cl-15.30%.
Found: C-52.08%; H-6.05%; N-5.84%; Cl-15.27%.

Example H

Benzyl-4-chloro-5-formyl-2,3,6,7-tetrahydro-1H-1-azepinecarboxylate

This compound was prepared from 40 gm (0.16 mol) of 1-benzyl-4-chloro-5-formyl-2,3,6,7-tetrahydro-1H-azepine and 34.2 gm (0.20 mol) of benzyl chloroformate analogous to Example G.

Yield: 95% of theory.

Calc.: molecular peak m/e=293/295 (1 Cl). Found: molecular peak m/e=293/295 (1 Cl).

Example I

4-Chloro-5-formyl-2,3,6,7-tetrahydro-1H-azepine hydrobromide 10.5 gm (0.036 mol) of benzyl 4-chloro-5-formyl-2,3,6,7-tetrahydro-1H-1-azepine-carboxylate were mixed with 100 ml of a 40% solution of hydrogen bromide in glacial acetic acid, while stirring and cooling with ice. The mixture was then stirred for 3 hours at room temperature. It was then concentrated by evaporation in a rotary evaporator, and the residue was triturated with ether. After the ether had been decanted several times, the product was suction-filtered and washed twice with absolute ether.

Yield: 8.0 gm (93% of theory).
Melting point: 204°–206° C.

Example J

Benzyl 4-chloro-5-cyano-2,3,6,7-tetrahydro-1H-azepine-1-carboxylate 4.3 gm=3.9 ml (0.025 mol) of benzyl chloroformate dissolved in 15 ml of methylene chloride, were added dropwise to a solution of 4.9 gm (0.02 mol) of 1-benzyl-4-chloro-5-cyano-2,3,6,7-tetrahydro-1H-azepine in 500 ml of methylene chloride while stirring at room temperature, whereby the temperature rose by 5° C. The mixture was stirred for 5 hours at room temperature and then allowed to stand overnight. The solvent was then removed in a rotary evaporator, and the residue was purified on a silicagel column (toluene/ethyl acetate=8:2). After the corresponding fractions had been concentrated by evaporation, a slightly yellowish oil was obtained with solidified upon standing.

Yield: 5.3 gm (91% of theory).
Melting point: 48°–50° C.
Calc.: C-61.96%; H-5.20%; N-9.64%; Cl-12.19%. Found: C-61.84%; H-5.07%; N-9.47%; Cl-12.07%.

Example K

4-Chloro-5-cyano-2,3,6,7-tetrahydro-1H-azepine hydrochloride 1.45 gm (0.005 mol) of benzyl 4-chloro-5-cyano-2,3,6,7-tetrahydro-1H-1-azepine-carboxylate were dissolved in 20 ml of ethyl alcohol by addition of 0.9 ml of semiconcentrated hydrochloric acid, and after the addition of 0.2 gm of palladium-on-charcoal, the mixture was hydrogenated in an autoclave at room temperature and under a hydrogen pressure of 5 bars. After half an hour, the uptake of hydrogen had ended. The catalyst was filtered off, and the filtrate was evaporated in vacuo. The residue was recrystallized from isopropyl alcohol.

Yield: 0.5 gm (52% of theory).
Melting point: 203°–205° C.
Calc.: C-43.54%; H-5.22%; N-14.51%. Found: C-43.98%; H-5.23%; N-14.39%.

Example L

1-Ethyl-4-chloro-5-cyano-2,3,6,7-tetrahydro-1H-azepine 7.1 gm (0.037 mol) of 4-chloro-5-cyano-2,3,6,7-tetrahydro-1H-azepine hydrochloride were dissolved in 170 ml of chloroform by addition of 28.5 ml of triethylamine. Then, 8.6 gm (0.055 mol)=4.9 ml of ethyl iodide were added dropwise at the boiling point, while stirring, and the mixture was refluxed for 4 hours. To complete the reaction, another 10 ml of triethylamine and 2.5 ml of ethyl iodide were added, and the mixture was boiled further. After a total of 10 hours the reaction was finished. After standing overnight, the mixture was concentrated by evaporation in vacuo. The residue was chromatographed on a silica-gel column (chloroform/methyl alcohol/ammonia=9:1:0.1). After the corresponding fractions had been concentrated by evaporation, the mixture was evaporated in vacuo.

Yield: 4.0 gm (59% of theory).
Calc.: molecular peak m/e=184/186 (1 Cl). Found: molecular peak m/e=184/186 (1 Cl).

Example M

1-Ethyl-4-chloro-5-cyano-2,3,6,7-tetrahydro-1H-azepine

This compound was prepared from 1-ethyl-4-chloro-2,3,6,7-tetrahydro-5-oximinomethylene-1H-azepine and phosphorus oxychloride analogous to Example E.

Yield: 63.2% of theory.
Calc.: molecular peak m/e=184/186 (1Cl). Found: molecular peak m/e=184/186 (1 Cl).

Example N 1-(2-Chlorobenzyl)-4-chloro-5-formyl-2,3,6,7-tetrahydro-1H-azepine hydrochloride This compound was prepared analogous to Example A from 1-(2-chlorobenzyl)-hexahydro-azepinone-(4) hydrochloride by the Vilsmeier reaction with dimethylformamide/phosphorus oxychloride.

Yield: 42% of theory.
Melting point: 202°–204° C.
Calc.: C-52.44%; H-5.03%; Cl-33.17%; N-4.37%.
Found: C-52.55%; H-5.08%; Cl-32.65%; N-4.50%.

Example O

1-Benzyl-3-chloro-4-formyl-2,5,6,7-tetrahydro-1H-azepine hydrochloride

This compound was prepared analogous to Example A from 1-benzyl-hexahydro-azepinone-(3) hydrochloride by the Vilsmeier reaction with dimethylformamide/phosphorus oxychloride.

Yield: 31% of theory.
Melting point: 133° C. (decomp.).
Calc.: C-58.76%; H-5.99%; Cl-24.77%; N-4.90%.
Found: C-59.10%; H-5.81%; Cl-25.00%; N-4.91%.

Preparation of the End Products of the Formula I

EXAMPLE 1

Ethyl 6-benzyl 5,6,7,8-tetrahydro-4H-thieno[2,3-d]-azepine-2-carboxylate

A suspension of 85.3 gm (0.298 mol) of 1-benzyl-4-chloro-5-formyl-2,3,6,7-tetrahydro-1H-azepine hydrochloride in 350 ml of pyridine was mixed at room temperature with 43 gm (0.358 mol) of ethyl thioglycolate. Within 1½ hours, 75 gm (0.75 mol) of absolute triethylamine were added dropwise while stirring, and gradually a solution was formed. The temperature was kept below 35° C. by cooling with ice-cold water. Then, the mixture was stirred for 3 hours at room temperature and allowed to stand overnight. 80 ml of an aqueous 48% potassium hydroxide solution were then added slowly dropwise, while vigorously stirring and cooling with ice, and the mixture was stirred for 2 hours while being cooled with ice. The reaction mixture was then poured into ice-cold water, and the oil initially precipitated crystallized out after some time. The crystals were suction-filtered off, washed several times with water and recrystallized from a little isopropyl alcohol.

Yield: 68 gm (72% of theory).
Melting point: 65°–66° C.
Calc.: C-68.54%; H-6.71%; N-4.44%; S-10.17%.
Found: C-68.76%; H-6.92%; N-4.42%; S-10.05%.

Example 2

Ethyl 5,6,7,8-tetrahydro-4H-thieno[2,3-d]azepine-2-carboxylate hydrochloride 15.4 gm (0.049 mol) of ethyl 6-benzyl-5,6,7,8-tetrahydro-4H-thieno[2,3-d]-azepine-2-carboxylate were dissolved in 200 of ethyl alcohol by the addition of 50 ml of 1 N hydrochloric acid. After the addition of 5 gm of palladium oxide, the mixture was hydrogenated in an autoclave for 3 hours at 80° C. and under a hydrogen pressure of 5 bars. After the reaction mixture had been cooled, the catalyst was filtered off, the filtrate was evaporated, and the residue was triturated with acetone. The product was suction-filtered and washed several times with acetone.

Yield: 12.8 gm (91% of theory).
Melting point: 159°–160° C.
Calc.: C-50.47%; H-6.17%; N-5.35%; Cl-13.54%; S-12.25%. Found: C-50.63%; H-6.40%; N-5.23%; Cl-13.56%; S-12.15%.

Example 3

Ethyl 6-ethyl-5,6,7,8-tetrahydro-4H-thieno[2,3-d]azepine-2-carboxylate hydrochloride 6.9 gm (0.0306 mol) of ethyl-5,6,7,8-tetrahydro-4H-thieno[2.3-d]azepine-2-carboxylate were dissolved in 60 ml of chloroform and 4.6 gm=6.4 ml (0.046 mol) of triethylamine, and the solution was heated to boiling. 5.5 gm=2.85 ml (0.035 mol) of ethyl iodide, dissolved in 10 ml of chloroform, were slowly added dropwise while stirring, and the mixture was heated for 3 hours more. After this time, another 1.3 ml of triethylamine and 0.57 ml of ethyl iodide were added. After another 2 hours of boiling, the same compounds were added again in the same quantities. After a total of 7 hours of heating the reaction was finished. The reaction mixture was allowed to cool, and was then extracted three times with water and dried over sodium sulfate. After the chloroform phase had been concentrated by evaporation in a rotary evaporator, 8 gm of a brown oil remained. By dissolving the oil in acetone and mixing the solution with ethereal hydrochloric acid the hydrochloride was precipitated which was then suction-filtered off and recrystallized from isopropyl alcohol.

Yield: 5.6 gm (63.1% of theory).
Melting point: 198°–199° C.
Calc.: C-53.88%; H-6.96%; N-4.83%; Cl-12.23%; S-11.06%. Found: C-53.90%; H-7.06%; N-4.96%; Cl-12.40%; S-11.10%.

Example 4

Ethyl 6-ethyl-5,6,7,8-tetrahydro-4H-thieno[2,3-d]azepine-2-carboxylate 3.15 gm (0.01 mol) of ethyl 6-benzyl-5,6,7,8-tetrahydro-4H-thieno[2,3-d]azepine-2-carboxylate were refluxed with the same amount of Raney nickel in 50 ml of ethyl alcohol for 6 hours. The catalyst was then removed by suction filtering, and the filtrate was concentrated by evaporation.

Yield: 2.1 gm (66.6% of theory), yellow oil.
Calc.: molecular peak m/e=253. Found: molecular peak m/e=253.

Example 5

Diethyl 5,6,7,8-tetrahydro-4H-thieno[2,3-d]azepine-2,6-carboxylate and

Diethyl 5,6,7,8-tetrahydro-4H-thieno[3,2-c]azepine-2,5-dicarboxylate 92.5 gm (0.4 mol) of an isomer mixture consisting of ethyl 4-chloro-5-formyl-2,3,6,7-tetrahydro-1H-1-azepine carboxylate and ethyl 4-chloro-3-formyl-2,5,6,7-tetrahydro-1H-1-azepine carboxylate were dissolved in 400 ml of pyridine. After the addition of 57.5 g=52.5 ml (0.478 mol) of ethyl thioglycolate, 60 gm=82.5 ml (0.594 mol) of triethylamine were added dropwise within 1½ hours, accompanied by vigorous stirring and cooling with ice, while the temperature was kept below 25° C. The mixture was then stirred for another 4 hours and then allowed to stand overnight. On the next day, a solution of 33.5 gm (0.6 mol) of potassium hydroxide in 40 ml of water was slowly added dropwise while vigorously stirring and cooling. The temperature was not allowed to exceed 10° C. The mixture was then stirred for another hour. Then, the reaction mixture was poured into ice-cold water and extracted several times with ether, with the addition of some ethyl acetate. The combined extracts were extracted three times with water and dried over sodium sulfate. After the solvent had been distilled off in vacuo, a yellow oil was obtained which was purified by chromatography on a column of silica-gel (1.5 liters; toluene/acetone=19:1).

Yield: 71.5 gm (60% of theory).
Calc.: C-56.55%; H-6.44%; N-4.71%; S-10.78%.
Found: C-56.50%; H-6.52%; N-4.97%; S-10.82%.

The following isomer mixture was prepared analogously:

Ethyl 6-benzyloxycarbonyl-5,6,7,8-tetrahydro-4H-thieno-[2,3-d]azepine-2-carboxylate and
Ethyl 5-benzyloxycarbonyl-5,6,7,8-tetrahydro-4H-thieno[3,2-c]azepine-2-carboxylate.

Yield: 39.5% of theory, oil (2:1 mixture).
Calc.: C-63.49%; H-5.89%; N-3.90%; S-8.92%.
Found: C-63.68%; H-5.87%; N-3.83%; S-9.03%.

Example 6

6-Ethoxycarbonyl-5,6,7,8-tetrahydro-4H-thieno[2,3-d]azepine-2-carboxylic acid and 5-Ethoxycarbonyl-5,6,7,8-tetrahydro-4H-thieno[3,2-c]azepine-2-carboxylic acid 10 gm (0.034 mol) of an isomer mixture consisting of diethyl 5,6,7,8-tetrahydro-4H-thieno[2,3-d]azepine-2,6-dicarboxylate and diethyl 5,6,7,8-tetrahydro-4H- thieno[3,2-c]azepine-2,5-dicarboxylate were refluxed for 4 hours in a solution of 2.8 gm (0.05 mol) of potassium hydroxide in 150 ml of absolute ethyl alcohol. Then, the mixture was concentrated by evaporation in vacuo, the residue was taken up in water and extracted three times with ether. The ether extracts were discarded, and the aqueous phase was acidified with concentrated hydrochloric acid. It was extracted several times with ether, and the combined ether phases were washed with water and dried over sodium sulfate. After the ether had been distilled off, 9.2 gm of a yellowish oil remained.

To separate the isomers, the mixture was chromatographed on a silicagel column (1.3 liters, toluene/glacial acetic acid=9:1). The separation was monitored by thinlayer chromatography. After the fractions containing only one isomer had been combined, the solvent was distilled off.

Yield of the [2,3-d]isomer: 1.05 gm (11.6% of theory). Melting point: 170°–171° C.
Calc.: C-53.52%; H-5.61%; N-5.20%. Found: C-53.00%; H-5.63%; N-5.27%.

Yield of the [3,2-c]isomer: 3.05 gm (33.9% of theory). Melting point: 135°–137° C.
Calc.: C-53.52%; H-5.61%; N-5.20%; S-11.90%. Found: C-53.60%; H-5.74%; N-5.28%; S-12.20%.

EXAMPLE 7

Ethyl 5,6,7,8-tetrahydro-4H-thieno[2,3-d]azepine-2-carboxylate and

Ethyl 5,6,7,8-tetrahydro-4H-thieno[3,2-c]azepine-2-carboxylate 82.5 gm (0.275 mol) of an isomer mixture consisting of diethyl 5,6,7,8-tetrahydro-4H-thieno[2,3-d]azepine-2,6-dicarboxylate and diethyl 5,6,7,8-tetrahydro-4H-thieno-[3,2-c]azepine-2,5-dicarboxylate were added dropwise to a boiling solution of 154 gm (2.75 mols) of potassium hydroxide in 1.3 liters of absolute ethyl alcohol, while stirring, and the mixture was refluxed for an hour. Then, the ethanol formed was slowly distilled off. In order to remove all the alcohol, a vacuum was applied towards the end of the distillation. The dry residue, consisting of a mixture of the potassium salts of 5,6,7,8-tetrahydro-4H-thieno[2,3-d]-azepine-2-carboxylic acid and 5,6,7,8-tetrahydro-4H-thieno-[3,2-c]azepine-2-carboxylic acid was suspended in 1.3 liters of absolute ethanol, and hydrogen chloride was introduced, first at room temperature for three hours and then at reflux temperature for 1.5 hours. This procedure was repeated after the mixture had been allowed to stand for 48 hours. The mixture was then cooled, the precipitated potassium chloride was separated by suction filtering, and the filtrate was concentrated by evaporation in vacuo. The residue was dissolved in water, and the solution was extracted twice with ether. The aqueous phase was made alkaline with sodium carbonate and extracted three times with chloroform. After the combined chloroform extracts had been washed twice with water and dried over sodium sulfate, they were evaporated in vacuo.

Yield of isomer mixture: 22.6 gm (36% of theory).

To separate the isomers, 10 gm of the isomer mixture was chromatographed on a silicagel column (1.9 liter; chloroform/ethyl alcohol/ammonia=9/1.3/0.07). The separation was monitored by thin-layer chromatography. After the fractions containing only one isomer had been combined, the solvent was distilled off.

Yield of the [2,3-d]isomer: 3.3 gm (11.9% of theory).
Calc.: C-58.64%; H-6.71%; N-6.22%; S-14.20%. Found: C-58.32%; H-6.92%; N-6.39%; S-14.06%.

Yield of the [3,2-c]isomer: 4.7 gm (16.8% of theory).
Calc.: molecular peak m/e=225. Found: molecular peak m/e=225.

Melting point of the hydrochloride: 252° C. (decomp.).
Calc.: C-50.70%; H-6.17%; N-5.28%; Cl-13.35%; S-12.20%. Found: C-50.47%; H-6.16%; N-5.35%; Cl-13.54%; S-12.25%.

Example 8

6-Benzyl-5,6,7,8-tetrahydro-4H-thieno[2,3-d]azepine-2-carboxylic acid hydrochloride 21.5 gm (0.068 mol) of ethyl 6-benzyl-5,6,7,8-tetrahydro-4H-thieno[2,3-d]azepine-2-carboxylate were heated in 100 ml of concentrated hydrochloric acid on a steam bath, with the addition of 50 ml of water, whereby the substance gradually dissolved. After 1½ hours, another 20 ml of concentrated hydrochloric acid were added, and the mixture was heated for another 30 minutes. Thereafter, it was allowed to stand overnight, whereupon the precipitated product was suction-filtered off and recrystallized from ethanol.

Yield: 8.1 gm (37% of theory).
Melting point: 260°–262° C. decomp.).
Calc.: C-59.34%; H-5.60%; N-4.33%; Cl-10.95%; S-9.90%. Found: C-59.40%; H-5.76%; N-4.25%; Cl-11.10%; S10.00%.

The following compounds were prepared analogous to Example 1, with the corresponding 4-chloro-5-formyl compound not always being isolated as the intermediate product, and according to Examples 3, 7 and 8:

(a) Ethyl 6-ethyl-5,6,7,8-tetrahydro-4H-thieno[2,3-d]-azepine-2-carboxylate hydrochloride Yield: 22% of theory.
Melting point: 198°–199° C.

(b) 6-Ethyl-5,6,7,8-tetrahydro-4H-thieno[2,3-d]-azepine-2-carboxylate acid hydrochloride Yield: 51.3% of theory.
Melting point: 299° C. (decomp.).
Calc.: C-50.46%; H-6.16%; N-5.35%; Cl-13.54%; S-12.25%. Found: C-50.70%; H-6.26%; N-5.34%; Cl-13.68%; S-12.18%.

(c) Ethyl 6-allyl-5,6,7,8-tetrahydro-4H-thieno[2,3-d]-azepine-2-carboxylate hydrochloride Yield: 31% of theory.
Melting point: 196°–197° C.
Calc.: C-55.71%; H-6.68%; N-4.64%; Cl-11.74%. Found: C-55.70%; H-6.75%; N-4.63%; Cl-11.75%.

(d) 6-Allyl-5,6,7,8-tetrahydro-4H-thieno[2,3-d]azepine-2-carboxylic acid hydrochloride Yield: 44.4% of theory.
Melting point: 276° C. (decomp.).
Calc.: C-52.65%; H-5.89%; N-5.12%, Cl-12.95%; S-11.71%. Found: C-52.70%; H-5.99%; N-5.06%; Cl-13.00%; S-11.68%.

(e) Ethyl 6-allyl-5,6,7,8-tetrahydro-4H-thieno[2,3-d]-azepine-2-carboxylate

Yield: 81% of theory; brown oil.
Calc. C-63.36%; H-7.22%; N-5.28%. Found: C-63.19%; H-7.34%; N-5.51%.

(f) Ethyl 6-(2-chlorobenzyl)-5,6,7,8-tetrahydro-4H-thieno-[2,3-d]-azepine-2-carboxylate hydrochloride Yield: 76.6% of theory.
Melting point: 191°–192° C.
Calc.: C-55.96%; H-5.48%; N-3.62%; Cl:18.35%; S-8.30%. Found: C-56.20%; H-5.46%; N-3.66%; Cl-18.55%; S-8.45%.

(g) 6-(2-Chlorobenzyl)-5,6,7,8-tetrahydro-4H-thieno[2,3-d]-azepine-2-carboxylic acid hydrochloride
Yield: 71.9% of theory.
Melting point: 247°–248° C.
Calc.: C-53.64%; H-4.78%; N-3.91%; Cl-19.79%; S-8.95%. Found: C-53.60%; H-4.74%; N-3.90%; Cl-19.65%; S-8.76%.

(h) Ethyl 6-(4-chlorobenzyl)-5,6,7,8-tetrahydro-4H-thieno-[2,3-d]-azepine-2-carboxylate
Yield: 79% of theory.
Melting point: 89°–90° C.
Calc.: C-61.79%; H-5.76%; N-4.00%; Cl-10.13%; S-9.16%. Found: C-61.70%; H-5.78%; N-3.98%; Cl-10.30%; S-9.15%.

(i) 6-(4-chlorobenzyl)-5,6,7,8-tetrahydro-4H-thieno-[2,3-d]azepine-2-carboxylic acid hydrochloride
Yield: 84.6% of theory. Melting point: 253°–254° C. (decomp.).
Calc.: C-53.64%; H-4.78%; N-3.91%; Cl-19.79%; S-8.95%. Found: C-53.80%; H-4.83%; N-3.84%; Cl-19.92%; S-8.98%.

(j) Sodium salt of 6-dodecyl-5,6,7,8-tetrahydro-4H-thieno-[2,3-d]azepine-2-carboxylic acid
Yield: 36.2% of theory.
Melting point: from 305° C. (decomp.).
Calc.: C-65.08%; H-8.84%; N-3.61%; S-8.27%. Found: C-65.30%; H-8.91%; N-3.45%; S-8.22%.

(k) Ethyl 6-(5-chloro-2-methoxy-benzoyl)-5,6,7,8-tetrahydro-4H-thieno[2,3-d]azepine-2-carboxylate
Yield: 21.6% of theory.
Melting point: 192°–193° C.
Calc.: C-57.94%; H-5.12%; N-3.56%; Cl-9.00%; S-8.14%. Found: C-58.30%; H-5.18%; N-3.61%; Cl-9.11%; S-8.16%.

(l) 6-(5-Chloro-2-methoxy-benzoyl)-5,6,7,8-tetrahydro-4H-thieno[2,3-d]azepine-2-carboxylic acid
Yield: 81.1% of theory.
Melting point: 234°–236° C.
Calc.: C-55.82%; H-4.41%; N-3.83%; S-8.76%. Found: C-56.00%; H-4.58%; N-3.90%; S-8.82%.

(m) Ethyl 5-(5-chloro-2-methoxy-benzoyl)-5,6,7,8-tetrahydro-4H-thieno[3,2-c]azepine-2-carboxylate
Yield: 26% of theory; oil.
Calc.: C-57.93%; H-5.12%; N-3.56%; S-8.14%; Cl-9.00%. Found: C-58.34%; H-4.99%; N-4.12%; S-7.76%; Cl-9.37%.

(n) 5-(5-Chloro-2-methoxy-benzoyl)-5,6,7,8-tetrahydro-4H-thieno[3,2-c]azepine-2-carboxylic acid
Yield: 74% of theory.
Melting point: 215°–216° C.
Calc.: C-55.82%; H-4.41%; N-3.83%; Cl-9.69%; S-8.76%. Found: C-55.60%; H-4.56%; N-3.82%; Cl-9.57%; S-8.53%.

(o) Ethyl 5,6,7,8-tetrahydro-6-propyl-4H-thieno[2,3-d]azepine-2-carboxylate
Yield: 93% of theory; oil.
Melting point of the hydrochloride: 222°–224° C.
Calc.: C-55.34%; H-7.30%; N-4.61%; Cl-11.67%; S-10.55%. Found: C-55.52%; H-7.17%; N-4.48%; Cl-11.83%; S-10.82%.

(p) Ethyl 5,6,7,8-tetrahydro-6-isopropyl-4H-thieno[2,3-d]azepine-2-carboxylate
Yield: 97% of theory; oil. Melting point of hydrochloride: 225°–227° C.
Calc.: C-55.34%; H-7.30%; N-4.61%; Cl-11.67%; S-10.55%. Found: C-55.35%; H-7.24%; N-4.59%; Cl-11.77%; S-10.77%.

(q) Ethyl 5,6,7,8-tetrahydro-6-methyl-4H-thieno[2,3-d]azepine-2-carboxylate
Yield: 42% of theory; oil. Melting point of the hydrochloride: 237°–239° C.
Calc.: C-52.26%; H-6.58%; N-5.08%; Cl-12.86%; S-11.62%. Found: C-52.36%; H-6.51%; N-5.21%; Cl-12.90%; S-11.90%.

(r) Ethyl 5-ethyl-5,6,7,8-tetrahydro-4H-thieno[3,2-c]azepine-2-carboxylate
Yield: 71.2% of theory; yellow oil.
Calc.: C-61.63%; H-7.56%; N-5.53;L %; S-12.65%. Found: C-61.45%; H-7.39%; N-5.77%; S-12.89%.

Example 9

Diethyl 2amino-5,6,7,8-tetrahydro-4H-thieno[2,3-c]azepine-3,7-dicarboxylate 3.7 gm (0.02 mol) of ethyl hexahydro-azepinone-(4)-1-carboxylate were suspended, together with 2,26 gm (0.02 mol) of ethyl cyanoacetate and 0.65 gm (0.02 mol) of sulfur, in 20 ml of ethyl alcohol. 5 ml of morpholine were added dropwise to this suspension, while stirring, whereby the temperature rose to about 30° C. The mixture was then stirred for 3 hours more at 50° C. and allowed to stand overnight at room temperature. On the next day, the solid product which had precipitated was suction-filtered off and recrystallized from isopropyl alcohol.
Yield: 3.6 gm (58% of theory).
Melting point: 104°–106° C.
Calc.: C-53.86%; H-6.41%; N-8.98%; S-10.25%. Found: C-53.90%; H-6.40%; N-9.04%; S-10.32%.

Example 10

Methyl 2-amino-5,6,7,8-tetrahydro-4H-thieno[2,3-d]azepine-3-carboxylate hydrochloride A solution of 41 gm (0.15 mol) of 5-bromo-hexahydroazepinone-(4) hydrobromide in 90 ml of methyl alcohol, was admixed dropwise with a solution of 11.1 gm (0.15 mol) of sodium hydrogen sulfide in 120 ml of methyl alcohol at 10° to 15° C. within 25 minutes. After 20 minutes of stirring at 10° to 15° C., 14.9 gm (0.15 mol) of methyl cyanoacetate were added. Then, 21.9 gm (0.3 mol) of diethylamine were added dropwise within 20 minutes, while vigorously stirring, whereby the internal temperature rose from 8° to 26° C. The mixture was then stirred for 2 hours more at 40° C. After cooling, it was concentrated by evaporation in vacuo, the residue was taken up in dilute sodium hydroxide and repeatedly extracted with chloroform. The chloroform phases were washed with dilute sodium hydroxide and water, dried over sodium sulfate and evaporated in vacuo. The residue was chromatographed on a silicagel column (chloroform/methanol/aqueous ammonia=7:4:0.25). The corresponding fractions were combined and evaporated in vacuo. The residue was taken up in methanol, and the hydrochloride was precipitated with isopropanolic hydrochloric acid and then suction-filtered off. The salt, which was difficult to dissolve, was boiled twice with methanol.
Yield: 5.4 gm (13.7% of theory).

Melting point: from 256° C. (decomp.).
Calc.: C-45.71%; H-5.75%; N-10.66%; Cl-13.49%; S-12.20%. Found: C-45.67%; H-5.81%; N-10.64%; Cl-13.50%; S-12.04%.

Example 11

Ethyl 3-amino-6-benzyl-5,6,7,8-tetrahydro-4H-thieno-[2,3-d]azepine-2-carboxylate 4.9 gm (0.020 mol) of 1-benzyl-4-chloro-5-cyano-2,3,6,7-tetrahydro-1H-azepine were refluxed for 5 hours with 2.5 gm (0.021 mol) of ethyl thioglycolate and 2.2 gm (0.021 mol) of sodium carbonate in 30 ml of ethanol, while stirring, and then the mixture was allowed to cool overnight. On the next day, the mixture was concentrated by evaporation in vacuo and the residue was taken up in a mixture of chloroform and water. The chloroform phase was washed three times with water, dried over sodium sulfate and concentrated by evaporation in vacuo. The residue was triturated with isopropyl alcohol, suction-filtered and recrystallized from isopropyl alcohol.

Yield: 4.6 gm (70% of theory).
Melting point: 101°–102° C.
Calc.: C-65.43%; H-6.71%; N-8.48%; S-9.70%;. Found: C-65.60%; H-6.33%; N-8.15%; S-9.74%.

The following compounds were prepared analogous to Examples 9, 10 and 11:

(a) Ethyl 2-amino-6-benzyl-5,6,7,8-tetrahydro-4H-thieno-[2,3-d]azepine-3-carboxylate hydrochloride
Yield: 23% of theory.
Melting point: 228°–229° C. (decomp.).
Calc.: C-58.93%; H-6.32%; N-7.63%; Cl-9.66%; S-8.74%. Found: C-58.64%; H-6.32%; N-7.36%; Cl-9.34%; S-8.52%.

(b) Ethyl 6-ethyl-2-amino-5,6,7,8-tetrahydro-4H-thieno-[2,3-d]azepine-3-carboxylate oxalate
Yield: 32% of theory.
Melting point: 173°–174° C. (decomp.).
Calc.: C-50.27%; H-6.19%; N-7.82%; S-8.94%. Found: C-50.25%; H-6.36%; N-7.64%; S-9.23%.

(c) Ethyl 6-allyl-2-amino-5,6,7,8-tetrahydro-4H-thieno-[2,3-d]azepine-3-carboxylate
Yield: 26.1% of theory; red oil.
Calc.: molecular peak m/e=280. Found: molecular peak m/e=280.

(d) Diethyl 2-amino-5,6,7,8-tetrahydro-4H-thieno-[2,3-d]-azepine-3, 6-dicarboxylate and Diethyl 2-amino-5,6,7,8-tetrahydro-4H-thieno-[2,3-c]azepine-3,7-dicarboxylate
Yield: 16.1% of theory.
Melting point: 122°–125° C.
Calc.: C-53.83%; H-6.45%; N-8.97%; S-10.26%. Found: C-54.00%; H-6.35%; N-9.16%; S-10.06%.

(e) Ethyl 6-ethyl-3-amino-5,6,7,8-tetrahydro-4H-thieno-[2,3-d]azepine-2-carboxylate
Yield: 89% of theory; light brown oil.
Calc.: molecular peak m/e=268. Found: molecular peak m/e=268.

Example 12

5,6,7,8-tetrahydro-6-propyl-4H-thieno[2,3-d]azepine-2-carboxylic acid hydrazide 13.0 gm (0.0486 mol) of ethyl 5,6,7,8-tetrahydro-6-propyl-4H-thieno[2,3-d]azepine-2-carboxylate were dissolved in 15 ml of absolute ethyl alcohol, and the solution was refluxed for 3 hours with 14 ml (0.23 mol) of 80% hydrazine hydrate. After cooling, the mixture was concentrated by evaporation in vacuo, and the residue was recrystallized from isopropyl alcohol.

Yield: 9.6 gm (78% of theory).
Melting point: 146°–148° C.
Calc.: C-56.89%; H-7.56%; N-16.58%; S-12.65%. Found: C-57.09%; H-7.62%; N-16.60%; S-12.75%.

Example 13

2-(N-tert. butoxycarbonylamino)-6-propyl-5,6,7,8-tetrahydro-4H-thieno[2,3-d]azepine 8.5 gm (0.0335 mol) of 5,6,7,8-tetrahydro-6-propyl-4H-thieno[2,3-d]azepine-2-carboxylic acid hydrazide were dissolved in 70 ml of 2 N hydrochloric acid and diazotized with a solution of 2.8 gm (0.04 mol) of sodium nitrite in 10 ml of water at $-5°$ to 0° C. The mixture was stirred for 50 minutes at 0° C., and the thick crystal slurry thus formed was mixed with 150 ml of methylene chloride. Then, 40 ml of concentrated ammonia were added dropwise, the methylene chloride phase was separated, and the aqueous phase was extracted several times with methylene chloride. The combined methylene chloride phases were dried over sodium sulfate and concentrated by evaporation in a rotary evaporator at a bath temperature of 30° C. Then, the product was mixed twice with benzene and after each time concentrated by evaporation in vacuo.

Yield of azide: 8.5 gm (95.8% of theory); light brown oil.

The substance (0.032 mol) was dissolved in 25 ml of absolute dioxane and, over a period of 30 minutes, the solution was added dropwise to a mixture of 30 ml of absolute dioxane and 2.9 gm (0.0385 mol) of tert. butyl alcohol which had been heated to 90° C., whereupon a vigorous evolution of nitrogen occurred. The mixture was then heated at its boiling point for 1½ hours and allowed to cool overnight. The next day it was concentrated by evaporation in vacuo, and the residue was chromatographed on a silicagel column (ethyl acetate-/ethyl alcohol/ammonium hydroxide=0.2:7:0.7). The corresponding fractions were combined and then concentrated by evaporation in vacuo.

Yield: 5.5 gm (55% of theory).
Melting point: 141°–143° C.

Example 14

2-(N-tert. butoxycarbonylamino)-6-(4-chlorobenzyl)-5,6,7,8-tetrahydro-4H-thieno[2,3-d]azepine A suspension of 5.7 gm (0.016 mol) of 6-(4-chlorobenzyl)-5,6,7,8-tetrahydro-4H-thieno[2,3-d]azepine-2-carboxylic acid hydrochloride in 90 ml of acetone and 3.7 gm (0.037 mol)=5.1 ml of triethylamine was stirred for 1½ hours at room temperature, and then a solution of 2.3 gm (0.021 mol) of ethyl chloroformate in 10 ml of acetone was added dropwise, while the temperature was maintained at 0° C. After 1½ hours of stirring at 0° C., a solution of 1.8 gm (0.027 mol) of sodium azide in 8 ml of water was added dropwise, and the mixture was stirred for 2 hours at 0° C. and then allowed to stand overnight at room temperature. The next day, the insoluble matter was filtered off, the filtrate was evaporated under mild conditions at a bath temperature of 30° C., and the residue was taken up in a mixture of methylene chloride and water. The methylene chloride phase was separated, washed three times with water, dried over sodium sulfate and evaporated in vacuo. In order to remove all the water, the product was dissolved in benzene, and the solution was concentrated by evaporation in vacuo.

Yield of azide: 5.4 gm (100% of theory); brown oil.

The substance (0.0156 mol) was dissolved in 30 ml of absolute dioxane with the addition of 1.35 gm (0.0182 mol) of absolute tert. butyl alcohol, and the solution was refluxed for 2 hours and then allowed to stand overnight at room temperature. It was then concentrated by evaporation in vacuo, and the resinous residue was chromatographed on a silicagel column (chloroform/acetone=9:1). After the corresponding fractions had been concentrated by evaporation, 3.7 gm of a semi-solid substance remained, which was digested with petroleum ether, suction-filtered off and washed again with petroleum ether.

Yield: 2.8 gm (44.8% of theory).
Melding point: 118°–119° C.
Calc.: C-61.14%; H-6.41%; N-7.13%; Cl-9.02%; S-8.16%; Found: C-61.40%; H-6.62%; N-7.10%; Cl-9.20%; S-8.30%.

Example 15

6-Ethyl-2-amino-5,6,7,8-tetrahydro-4H-thieno[2,3-]azepine dihydrobromide 2.0 gm (0.0068 mol) of 6-ethyl-2-(N-tert.butoxycarbonylamino)-5,6,7,8-tetrahydro-4H-thieno[2,3-d]azepine were added to 18 ml of a 40% glacial acetic acid hydrogen bromide solution, while dry nitrogen was introduced, accompanied by stirring and cooling to 0° C. After 3 hours of stirring at 0° C., 60 ml of absolute ether were added dropwise, and the mixture was stirred for 15 minutes and decanted. After the addition of absolute ether, followed by decanting, had been repeated several times, the initially sticky substance became crystalline and capable of being suction-filtered off. It was washed several times with absolute ether and dried over phosphorus pentoxide in a desiccator.

Yield: 1.8 gm (75% of theory).
Melting point: from 50° C. (decomp.).
Calc.: C-33.54%; H-5.07%; N-7.82%; Br-44.62%; S-8.95%. Found: C-33.80%; H-5.29%; N-7.36%; Br-44.30%; S-8.84%.

The following compounds were prepared analogous to Examples 12–15:

(a) 5,6,7,8-Tetrahydro-6-isopropyl-4H-thieno[2,3-d]azepine-2-carboxylic acid hydrazide
Yield: 76% of theory.
Melting point: 127°–129° C.
Calc.: C-56.89%; H-7.56%; N-16.58%; S-12.65%. Found: C-56.90%; H-7.44%; N-16.50%; S-12.45%.

(b) 2-(N-tert.-butoxycarbonylamino)-5,6,7,8-tetrahydro-6-isopropyl-4H-thieno[2,3-d]azepine
Yield: 38.5% of theory.
Calc.: C-61.90%; H-8.44%; N-9.02%; S-10.33%. Found: C-61.68%; H-8.56%; N-9.18%; S-10.19%.

(c) 2-Amino-5,6,7,8-tetrahydro-6-isopropyl-4H-thieno[2,3-d]azepine dihydrobromide
Yield: 83.5% of theory.
Calc.: C-35.50%; H-5.42%; N-7.53%; S-8.16%; Br-42.94%. Found: C-35.19%; H-5.63%; N-7.64%; S-8.32%; Br-42.51%.

(d) 6-Allyl-2-(N-tert.-butoxycarbonylamino)-5,6,7,8-tetrahydro-4H-thieno[2,3-d]azepine
Yield: 29.6% of theory.
Melting point: 135°–137° C.

Calc.: C-62.31%; H-7.84%; N-9.08%; S-10.39%. Found: C-62.40%; H-7.93%; N-9.06%; S-10.50%.

(e) 6-Allyl-2-amino-5,6,7,8-tetrahydro-4H-thieno[2,3-d]azepine dihydrobromide
Yield: 83.3% of theory.
Melting point: from 50° C. (decomp.).
Calc.: C-35.69%; H-4.90%; N-7.57%; Br-43.18%; S-8.66%. Found: C-35.70%; H-5.33%; N-6.95%; Br.42.70%; S-8.36%.

(f) 2-Amino-6-(4-chlorobenzyl)-5,6,7,8-tetrahydro-4H-thieno[2,3-d]azepine dihydrobromide
Yield: 75% of theory.
Melting point: from 225° C. (decomp.).
Calc.: molecular peak m/e=292/294 (1 Cl). Found: molecular peak m/e=292/294 (1 Cl).

(g) 6-Benzyl-2-(N-tert.-butoxycarbonylamino)-5,6,7,8-tetrahydro-4H-thieno[2,3-d]azepine
Yield: 45% of theory; yellow oil
Calc.: molecular peak m/e=358. Found: molecular peak m/e=358.

(h) 2-Amino-6-benzyl-5,6,7,8-tetrahydro-4H-thieno[2,3-d]azepine dihydrobromide
Yield: 84% of theory.
Melting point: 232°–234° C.
Calc.: C-42.87%; H-4.80%; N-6.67%; Br-38.03%; S-7.63%. Found: C-42.90%; H-4.87%; N-6.37%; Br-37.90%; S-7.80%.

(i) 6-Ethyl-2-(N-tert.butoxycarbonylamino)-5,6,7,8-tetrahydro-4H-thieno[2,3-d]azepine
Yield: 30.5% of theory.
Melting point: 149°–151° C.
Calc.: C-60.78%; H-8.16%; N-9.45%; S-10.82%. Found: C-61.00%; H-8.22%; N-9.40%; S-11.04%.

(j) 5-Ethyl-5,6,7,8-tetrahydro-4N-thieno[3,2-c]azepine-2-carboxylic acid hydrazide
Yield: 90% of theory.
Melting point: 134°–135° C.

(k) 5-Ethyl-2-(N-tert.butoxycarbonylamino)-5,6,7,8-tetrahydro-4H-thieno[3,2-c]azepine
Yield: 67.5% of theory.
Melting point: 154°–156° C.

(l) 5-Ethyl-2-amino-5,6,7,8-tetrahydro-4H-thieno[3,2-c]azepine dihydrobromide
Yield: 100% of theory (hygroscopic). Melting point: sintering from 100° C., from 210° C. (decomp.).

Example 16

6-Benzyl-5,6,7,8-tetrahydro-4H-thieno[2,3-d]azepine hydrochloride 3.1 gm (0.096 mol) of 6-benzyl-5,6,7,8-tetrahydro-4H-thieno[2,3-d]azepine-2-carboxylic acid hydrochloride were refluxed for 48 hours in 30 ml of concentrated hydrochloric acid. After cooling, the reaction mixture was concentrated by evaporation in vacuo, the residue was mixed with water, and the aqueous solution was made alkaline with 6 N sodium hydroxide solution and extracted several times with ether. The ether phases were again washed with water, dried over sodium sulfate and concentrated by evaporation in vacuo. After evaporating again with benzene, a brown oil remained which was dissolved in isopropyl alcohol. The hydrochloride was precipitated with isopropanolic hydrochloric acid and then recrystallized from isopropyl alcohol.

Yield: 1.8 gm (67% of theory).
Melting point: 237°–239° C.

Calc.: C-64.38%; H-6.48%; N-5.01%; Cl-12.67%; S-11.46%. Found: C-64.20%; H-6.60%; N-4.88%; Cl-12.70%; S-11.70%.

Example 17

6-(2-Chlorobenzyl)-5,6,7,8-tetrahydro-4H-thieno[2,3-d]azepine hydrochloride 6.9 gm (0.045 mol) of 5,6,7,8-tetrahydro-4H-thieno[2,3-d]azepine were refluxed for 10 hours with 5.6 gm=8.4 ml (0.055 mol) of absolute triethylamine and 7.97 gm=6.2 ml (0.0495 mol) of o-chlorobenzyl chloride in 120 ml of toluene, and after 5 hours a second batch of 1.6 gm of o-chlorobenzyl chloride and 1.2 gm of absolute triethylamine were added. After cooling, the reaction solution was washed several times with water and dried over sodium sulfate. After evaporation in vacuo, a yellow oil remained, which was chromatographed on a silicagel column (toluene/acetone=25:1). After evaporation of the corresponding fractions, the residue was dissolved in isopropyl alcohol, and the hydrochloride was precipitated with isopropanolic hydrochloric acid, suction-filtered off and recrystallized from isopropyl alcohol.

Yield: 6.8 gm (48% of theory).
Melting point: 195°–197° C.
Calc.: C-57.33%; H-5.45%; N-4.46%; Cl-22.56%; S-10.20% Found: C-57.54%; H-5.52%; N-4.48%; Cl-22.50%; S-10.32%.

The following compounds were prepared analogous to Examples 16 and 17:

(a) 6-Allyl-5,6,7,8-tetrahydro-4H-thieno[2,3-d]azepine hydrochloride
Yield: 23.8% of theory.
Melting point: 204°–206° C.
Calc.: C-57.50% H-7.02%; N-6.10%; Cl-15.43%; S-13.95%. Found: C-57.40%; H-6.94%; N-6.13%; Cl-15.55%; S-14.05%.

(b) 6-Ethyl-5,6,7,8-tetrahydro-4H-thieno[2,3-d]azepine hydrochloride
Yield: 33% of theory.
Melting point: 231°–234° C.
Calc.: C-55.16%; H-7.41%; N-6.43%; Cl-16.28%; S-14.72%. Found: C-54.90%; H-7.50%; N-6.45%; Cl-16.05%; S-14.87%.

(c) 5,6,7,8-Tetrahydro-4H-thieno[2,3-d]azepine hydrochloride
Yield: 32% of theory.
Melting point: 211°–213° C.
Calc.: C-50.65%; H-6.38%; N-7.38%; Cl-18.69%; S-16.90%. Found: C-50.70%; H-6.40%; N-7.38%; Cl-18.60%; S-16.80%.

(d) 5,6,7,8-Tetrahydro-4H-thieno[3,2-c]azepine hydrochloride
Yield: 35.3% of theory.
Melting point: 130°–132° C.
Calc.: C-50.65%; H-6.38%; N-7.38%; Cl-18.69%; S-16.90%. Found: C-50.75%; H-6.50%; N-7.48%; Cl-18.75%; S-16.75.

(e) 5-(2-Chlorobenzyl)-5,6,7,8-tetrahydro-4H-thieno[3,2-c]azepine hydrochloride
Yield: 45.4% of theory.
Melting point: 198°–200° C.
Calc.: C-57.33%; H-5.45%; N-4.46%; Cl-22.56%; S-10.20%. Found: C-57.20%; N-5.50%; N-4.46%; Cl-22.50%; S-10.18%.

(f) 6-(2-Chlorobenzoyl)-5,6,7,8-tetrahydro-4H-thieno[2,3-d]azepine

Yield: 75% of theory.
Melting point: 113°–115° C.
Calc.: C-61.74%; H-4.84%; N-4.80%; Cl-12.15%; S-10.99%. Found: C-61.84%; H-4.97%; N-4.88%; Cl-12.17%; S-11.00%.

Example 18

Methyl 4-[2-(6-benzyl-5,6,7,8-tetrahydro-4H-thieno[2,3-d]azepine-2-carboxamido)-ethyl]-benzoate 6 gm (0.05 mol) of thionyl chloride were added dropwise over a period of 5 minutes to a boiling suspension of 7.2 gm (0.025 mol) of 6-benzyl-5,6,7,8-tetrahydro-4H-thieno[2,3-d]azepine-2-carboxylic acid in 150 ml of chloroform, while stirring, and the mixture was refluxed for 45 minutes. At first, a clear solution was formed and then, after some time, a thick crystal slurry precipitated. The reaction mixture was cooled, and the crystal slurry was suction-filtered off, washed with chloroform and dried in a drying chamber at 100° C.

Yield: 7.3 gm (84.9% of theory). 3 g (0.03 mol) of absolute triethylamine were added, while stirring, at ambient temperature over a period of 10 minutes to a mixture of 3.4 gm (0.01 mol) of the 6-benzyl-5,6,7,8-tetrahydro-4H-thieno[2,3-d]azepine-2-carboxylic acid chloride hydrochloride thus obtained and 2.2 gm (0.01 mol) of methyl 4-(2-aminoethyl)-benzoate hydrochloride in 100 ml of chloroform. The mixture was then stirred for two hours and then allowed to stand for 60 hours at room temperature. The mixture was washed with water, then with dilute sodium carbonate and again with water, and the chloroform phase was separated and dried over sodium sulfate. After evaporation in vacuo to about 30 ml, the same amount of ether was added, and the mixture was allowed to crystallize and was then suction-filtered.

Yield: 3.8 gm (85.8% of theory).
Melting point: 210°–212° C.
Calc.: C-69.62%; H-6.29%; N-6.26%; S-7.15%. Found: C-69.51%; H-6.30%; N-6.26%; S-7.29%.

The following compound was prepared analogously:
(a) Ethyl 4-(6-benzyl-5,6,7,8-tetrahydro-4H-thieno[2,3-d]azepine-2-carboxamido)-benzoate
Yield: 43.8% of theory.
Melting point: 193°–195° C.
Calc.: C-69.10%; H-6.03%; N-6.45%; S-7.38%. Found: C-68.99%; H-6.11%; N-6.65%; S-7.55%.

EXAMPLE 19

4-[2-(6-Benzyl-5,6,7,8-tetrahydro-4H-thieno[2,3-d]azepine-2-carboxamido)-ethyl]-benzoic acid 1.7 gm (0.0038 mol) of methyl 4-[2-(6-benzyl-5,6,7,8-tetrahydro-4H-thieno[2,3-d]azepine-2-carboxamido)-ethyl]-benzoate were refluxed for 1.5 hours in a solution of 6 ml (0.006 mol) of 1 N sodium hydroxide in 70 ml of ethyl alcohol. After cooling, the mixture was concentrated by evaporation in vacuo, the residue was mixed with 50 ml of water, and the aqueous mixture was made weakly acid with glacial acetic acid. The precipitate formed thereby was suction filtered off, dissolved in isopropyl alcohol, and the solution was mixed with 3 ml of 2 N hydrochloric acid. After evaporation in vacuo, the residue was taken up in 5 ml of 90% isopropyl alcohol, and the solution was mixed with 30 ml of acetone. After standing overnight, the product was suction-filtered off and dried.

Yield: 1.2 gm (67.4% of theory).

Melting point: from 227° C. (decomp.).
Calc.: C-63.75%; H-5.78%; N-5.95%; Cl-7.53%; S-6.81%. Found: C-62.90%; H-5.86%; N-5.85%; Cl-7.24%; S-6.50%.

The following compound was prepared analogously:
(a) 4-(6-Benzyl-5,6,7,8-tetrahydro-4H-thieno[2,3-d]azepine-2-carboxamido)-benzoic acid hydrochloride.
Yield: 89.7% of theory.
Melting point: from 290° C. (decomp.).
Calc.: C-62.36%; H-5.23%; N-6.32%; Cl-8.00%; S-7.24%. Found: C-62.82%; H-5.34%; N-6.32%; Cl-8.01%; S-7.31%.

Example 20

6-(2,6-Dichlorobenzyl)-5,6,7,8-tetrahydro-4H-thieno[2,3-d]azepine hydrochloride

This compound was prepared analogous to Example 17 from 5,6,7,8-tetrahydro-4H-thieno[2,3-d]azepine and 2,6-dichlorobenzyl bromide.
Yield: 58% of theory.
Melting point: 213° C.
Calc.: C-51.66%; H-4.62%; Cl-30.50%; N-4.02%; S-9.19%. Found: C-51.73%; H-4.48%; Cl-30.60%; N-4.00%; S-9.14%.

Example 21

6-(2,4-Dichlorobenzyl)-5,6,7,8-tetrahydro-4H-thieno[2,3]azepine hydrochloride

This compound was prepared analogous to Example 17 from 5,6,7,8-tetrahydro-4H-thieno[2,3-d]azepine and 2,3-dichlorobenzyl chloride.
Yield: 56% of theory.
Melting point: 181°-182° C.
Calc.: C-51.66%; H-4.62%; Cl-30.50%; N-4.02%; S-9.19%. Found: C-51.90%; H-4.47%; Cl-30.10%; N-3.93%; S-9.25%.

Example 22

Ethyl 3-amino-6-benzyl-5,6,7,8-tetrahydro-4H-1-methylpyrrolo[2,3-d]-azepine-2-carboxylate 1.24 gm (0.005 mol) of 1-benzyl-4-chloro-5-cyano-2,3,6,7-tetrahydro-1H-azepine were heated at 100° C. with 1.53 gm (0.01 mol) of ethyl N-methylaminoacetate hydrochloride and 1.60 gm (0.015 mol) of anhydrous sodium carbonate in 10 ml of dimethylformamide for 5 hours, while stirring. After cooling, the reaction mixture was poured into ice-cold water, and the aqueous mixture was extracted several times with chloroform. The combined chloroform extracts were washed four times with water, dried over sodium sulfate and concentrated by evaporation. The residue was purified by chromatography on a silicagel column, using ethyl acetate/ethanol/petroleum ether (9/1/3) as eluant.
Yield: 0.8 gm of oil (49% of theory).
Calc.: molecular peak m/e=327. Found: molecular peak m/e=327.
Analysis of the hydrochloride: Calc.: C-57.00%; H-6.80%; N-10.50%. Found: C-56.60%; H-6.87%; N-10.43%.

Example 23

Ethyl 6-benzyl-5,6,7,8-tetrahydro-4H-1-methyl-pyrrolo[2,3-d]azepine-2-carboxylate hydrochloride 8.6 gm (0.03 mol) of 1-benzyl-4-chloro-5-formyl-2,3,6,7-tetrahydro-1H-azepine hydrochloride were stirred with 9.2 gm (0.06 mol) of ethyl N-methylaminoacetate hydrochloride and 12.7 gm (0.12 mol) of anhydrous sodium carbonate in 90 ml of absolute dimethylsulfoxide for 1½ hours at 40° C. The mixture was then poured into about 300 ml of ice-cold water, and the aqueous mixture was extracted twice with ethyl acetate. The combined extracts were washed three times with water, dried over sodium sulfate and concentrated by evaporation. The oily red residue thus obtained (5.8 gm ≙ 0.0175 mol) was dissolved in 20 ml of absolute dimethylformamide, and the solution was slowly added dropwise to a solution of 2.05 gm (0.0175 mol) of potassium tert. butoxide in 15 ml of absolute dimethylformamide at 5°-10° C. in a nitrogen atmosphere. After ½ hour of stirring at room temperature, the gel-like reaction solution was poured into ice-cold water, and the aqueous mixture was extracted several times with ethyl acetate. The combined organic phases were washed four times with water, dried over sodium sulfate and concentrated by evaporation. The residue was puridied by column chromatography on silicagel with toluene/ethanol=19:1 as eluant.
Yield: 3.4 gm (36% of theory).
Melting point: <20° C.
The product was dissolved in ethyl acetate, and the hydrochloride was precipitated with ethereal hydrochloric acid, suction-filtered off and recrystallized from ethyl acetate/isopropyl alcohol (9:1).
Melting point: 202°-203° C. (decomp.).
Calc.: C-65.41%; H-7.22%; Cl-10.16%; N-8.03%. Found: C-65.40%; H-7.20%; Cl-9.97%; N-8.09%.

Example 24

Ethyl 6-benzyloxycarbonyl-5,6,7,8-tetrahydro-4H-1-methyl-pyrrolo[2,3-d]azepine-2-carboxylate This compound was prepared analogous to Example 23 from benzyl-4-chloro-5-formyl-2,3,6,7-tetrahydro-1H-azepine carboxylate and ethyl N-methylaminoacetate hydrochloride.
Yield: 8% of theory.
Melting point: 73°-74° C.
Calc.: C-67.00%; H-6.79%; N-7.86%. Found: C-67.49%; H-6.77%; N-7.69%.

Example 25

Ethyl 6-(2-chlorobenzyl)-5,6,7,8-tetrahydro-4H-1-methylpyrrolo[2,3-d]-azepine-2-carboxylate hydrochloride This compound was prepared analogous to Example 3 from ethyl-5,6,7,8-tetrahydro-4H-methyl pyrrolo[2,3-d]azepine-2-carboxylate hydrochloride and 2-chlorobenzyl chloride.
Yield: 81% of theory.
Melting point: 169°-171° C.
Calc.: C-59.53%; H-6.31%; Cl-18.50%; N-7.31%. Found: C-59.47%; H-6.34%; Cl-18.60%; N-7.43%.

Example 26

Ethyl 6-ethyl-5,6,7,8-tetrahydro-4H-1-methyl-pyrrolo[2,3-d]azepine-2-carboxylate hydrochloride This compound was prepared analogous to Example 3 from ethyl 5,6,7,8-tetrahydro-4H-1-methyl-pyrrolo[2,3-d]azepine-2-carboxylate hydrochloride and ethyl iodide.

Yield: 62% of theory.
Melting point: 188°–189° C.
Calc.: C-58.63%; H-8.08%; Cl-12.36%; N-9.77%.
Found: C-58.40%; H-8.12%; Cl-12.35%; N-9.78%.

Example 27

Ethyl 6-(4-chlorobenzyl)-5,6,7,8-tetrahydro-4H-1-methylpyrrolo[2,3-d]azepine-2-carboxylate hydrochloride This compound was prepared analogous to Example 3 from ethyl 5,6,7,8-tetrahydro-4H-1-methyl-pyrrolo[2,3-d]azepine-2-carboxylate hydrochloride and 4-chlorobenzyl chloride.
Yield: 55% of theory.
Melting point: 185°–186° C.
Calc.: C-59.53%; H-6.31%; Cl-18.50%; N-7.31%.
Found: C-59.79%; H-6.65%; Cl-18.10%; N-7.14%.

Example 28

Ethyl 5,6,7,8-tetrahydro-4H-1-methyl-pyrrolo[2,3-d]azepine-2-carboxylate hydrochloride This compound was prepared analogous to Example 2 from ethyl 5,6,7,8-tetrahydro-4H-1-methyl-pyrrolo[2,3-d]azepine-2-carboxylate and catalytically activated hydrogen.
Yield: 84% of theory.
Melting point: 179°–180° C.
Calc.: C-55.70%; H-7.40%; Cl-13.70%; N-10.83%.
Found: C-55.84%; H-7.28%; Cl-13.45%; N-10.93%.

Example 29

6-Benzyl-5,6,7,8-tetrahydro-4H-1-methyl-pyrrolo[2,3-d]azepine-2-carboxylic acid 3.1 gm (0.01 mol) of ethyl 6-benzyl-5,6,7,8-tetrahydro-4H-1-methyl-pyrrolo[2,3-d]azepine-2-carboxylate were dissolved in 80 ml of ethanol with the addition of 10 ml of 2 N aqueous sodium hydroxide, and the solution was refluxed for 6 hours. The reaction mixture was concentrated by evaporation, and the residue was purified by column chromatography on silicagel with chloroform/methanol (8.5/1.5) as eluant.
Yield: 0.8 gm (28% of theory).
Melting point: 149°–150° C. (decomp.).
Calc.: C-71.81%; H-7.09%; N-9.85%. Found: C-71.94%; N-6.88%; N-10.09%.

Example 30

6-(2-Chlorobenzyl)-5,6,7,8-tetrahydro-4H-1-methyl-pyrrolo[2,3-d]azepine hydrochloride The sodium salt obtained analogous to Example 29 by hydrolysis of 3.3 gm (0.0095 mol) of ethyl 6-(2-chlorobenzyl)-5,6,7,8-tetrahydro-4H-1-methyl-pyrrolo[2,3-d]azepine-2-carboxylate was refluxed for 8 hours with 3.1 gm (0.035 mol) of oxalic acid in 50 ml of propanol. The mixture was then concentrated by evaporation, the residue was stirred with water, and the aqueous mixture was made alkaline with 2 N aqueous sodium hydroxide. After extracting three times with chloroform, the combined organic phases were washed with water, dried over sodium sulfate and concentrated by evaporation. The residue was purified by column chromatography on silica gel, using toluene/ethyl acetate/ethanolic ammonia (9/1/0.05) as eluant. The yellowish oil remaining after the solvent had been evaporated was dissolved in absolute ether, and then the hydrochloride was precipitated with ethereal hydrochloric acid. After suction-filtering, the hydrochloride was purified by precipitation with ether from hot isopropanol.
Yield: 1.9 gm (64% of theory).
Melting point: 179°–180° C.
Calc.: C-61.74%; H-6.48%; Cl-22.78%; N-9.00%.
Found: C-61.67%; H-6.46%; Cl-22.55%; N-8.99%.

Example 31

6-Benzyl-5,6,7,8-tetrahydro-4H-1-methyl-pyrrolo[2,3-d]azepine oxalate

This compound was prepared analogous to Example 30 from ethyl 6-benzyl-5,6,7,8-tetrahydro-4H-1-methyl-pyrrolo[2,3-d]azepine-2-carboxylate by hydrolysis and decarboxylation.
Yield: 64% of theory.
Melting point: 182°–183° C.
Calc.: C-65.44%; H-6.71%; N-8.48%. Found: C-65.54%; H-6.76%; N-8.44%.

Example 32

6-(4-Chlorobenzyl)-5,6,7,8-tetrahydro-4H-1-methyl-pyrrolo[2,3-d]azepine oxalate

This compound was prepared analogous to Example 30 from ethyl 6-(4-chlorobenzyl)-5,6,7,8-tetrahydro-4H-1-methyl-pyrrolo[2,3-d]azepine-2-carboxylate by hydrolysis and decarboxylation.
Yield: 29% of theory.
Melting point: 195°–196° C.
Calc.: C-59.26%; H-5.80%; Cl-9.72%; N-7.68%.
Found: C-59.20%; H-5.86%; Cl-9.56%; N-7.51%.

Example 33

5,6,7,8-Tetrahydro-4H-1-methyl-pyrrolo[2,3-d]azepine oxalate

This compound was prepared analogous to Example 30 from ethyl 5,6,7,8-tetrahydro-4H-1-methyl-pyrrolo[2,3-d]azepine-2-carboxylate by hydrolysis and decarboxylation.
Yield: 29% of theory.
Melting point: 180°–181° C.
Calc.: C-54.99%; H-6.71%; N-11.66%. Found: C-55.18%; H-6.75%; N-11.36%.

Example 34

Ethyl 7-benzyl-5,6,7,8-tetrahydro-4H-thieno[2,3-c]azepine-2-carboxylate

This compound was prepared analogous to Example 1 from 1-benzyl-3-chloro-4-formyl-2,5,6,7-tetrahydro-1H-azepine hydrochloride and thioglycol ester.
Yield: 19% of theory.
Melting point: 62°–63° C.
Calc.: molecular peak m/e=315. Found: molecular peak m/e=315.
Calc.: C-68.54%; H-6.71%; N-4.44%; S-10.17%.
Found: C-68.30%; H-6.65%; N-4.53%; S-10.22%.

Example 35

Butyl 6-(2-chlorobenzyl)-5,6,7,8-tetrahydro-4H-furo[2,3-d]azepine-2-carboxylate 2.0 gm (0.015 mol) of butyl glycolate were slowly added dropwise, while vigorously stirring, to a suspension of 0.72 gm (0.015 mol) of 50% sodium hydride in 10 ml of absolute dioxane at room temperature while dry nitrogen was introduced. The temperature of the intensely foaming reaction mixture was kept below 30° C. by cooling with ice-cold water, as needed. After 1½ hours of stirring at room temperature, a solution of 2.84 gm (0.010 mol) of 1-(2-chlorobenzyl)-4-chloro-5-formyl-2,3,6,7-tetrahydro-1H-azepine in 20 ml of absolute dioxane was added dropwise, whereupon the temperature of the reaction mixture rose from 20° C. to about 33° C. Then, the mixture was stirred for two hours at room temperature, poured into about 150 ml of ice-cold water, and the aqueous mixture was extracted three times with ethyl acetate. The combined organic phases were extracted with water three times, dried over sodium sulfate and concentrated by evaporation. The residue was purified by column chromatography on silicagel, using chloroform/ethyl acetate (93:7) as eluant.

Yield: 0.2 gm (6% of theory).
Melting point: 58° C.
Calc.: C-66.38%; H-6.68%; Cl-9.80%; N-3.87%.
Found: C-66.31%; H-6.50%; Cl-9.93%; N-3.78%.

Example 36

Butyl 3-amino-6-benzyl-5,6,7,8-tetrahydro-4H-furo[2,3-d]azepine-2-carboxylate

A solution of 1.0 gm (0.008 mol) of butyl glycolate in 8 ml of absolute dioxane was added dropwise to a suspension of 0.4 gm (0.008 mol) of 50% sodium hydride in 5 ml of absolute dioxane, and the mixture was stirred for one hour at room temperature. Then, while the mixture was cooled with ice, a solution of 1.0 gm (0.004 mol) of 1-benzyl-4-chloro-5-cyano-2,3,6,7-tetrahydro-1H-azepine in 15 ml of absolute dioxane was added, and the mixture was stirred for one hour. The reaction mixture was then poured into about 80 ml of ice-cold water, and the aqueous mixture was extracted three times with ethyl acetate. The combined organic phases were washed twice with water, dried over sodium sulfate and concentrated by evaporation. The residue was purified by column chromatography on silicagel, using toluene/ethyl acetate (7:3) as eluant.

Yield: 0.2 gm (14% of theory).
Melting point: <20° C.
Calc.: molecular peak m/e=342. Found: molecular peak m/e=342.

Example 37

6-(2-Chlorobenzyl)-5,6,7,8-tetrahydro-4H-furo[2,3-d]azepine-2-carboxylic acid

This compound was prepared analogous to Example 29 by hydrolysis of butyl 6-(2-chlorobenzyl)-5,6,7,8-tetrahydro-4H-furo[2,3-azepine-2-carboxylate with aqueous sodium hydroxide in ethanol.

Yield: 65% of theory.
Melting point: 120° C. (decomp., sintering from 200° C.).
Calc.: molecular peak m/e=305/307 (1 Cl). Found: molecular peak m/e=305/307 (1 Cl).
Calc.: C-62.85%; H-5.27%; Cl-11.60%; N-4.58%.
Found: C-62.66%; H-5.35%; Cl-11.39%; N-4.71%.

Example 38

6-(2-Chlorobenzyl)-5,6,7,8-tetrahydro-4H-furo[2,3-d]azepine

This compound was prepared analogous to Example 30 from 6-(2-chlorobenzyl)-5,6,7,8-tetrahydro-4H-furo[2,3-d]azepine-2-carboxylic acid by decarboxylation.

Yield: 35% of theory.
Melting point: <20° C.
Calc.: molecular peak m/e=261-263 (1 Cl). Found: molecular peak m/e=261-263 (1 Cl).
Calc.: C-68.83%; H-6.16%; Cl-13.54%; N-5.35%.
Found: C-68.79%; H-6.33%; Cl-13.36%; N-5.62%.

The compounds of the present invention, that is, those embraced by formula I above and their non-toxic, pharmacologically acceptable salts formed with inorganic or organic acids or bases, have useful pharmacodynamic properties. More particularly, they exhibit an inhibiting effect on the aggregation of tumor cells, especially antithrombotic activity, and an effect on intermediate metabolism, especially a lipid-reducing effect, in warm-blooded animals such as rats.

The above pharmacological properties of the compounds of this invention were ascertained by the methods described below, and Tables I to V show the results obtained for a few representative species of the genus, where A = 6-Benzyl-5,6,7,8-tetrahydro-4H-thieno[2,3-d]azepine-2-carboxylic acid hydrochloride,
B = Sodium 6-dodecyl-5,6,7,8-tetrahydro-4H-thieno[2,3-d]azepine-2-carboxylate and
C = 6-(2-Chlorobenzyl)-5,6,7,8-tetrahydro-4H-thieno[2,3-d]azepine hydrochloride.

1. Cholesterol-reducing effect (a) Test on the hyperlipemic rat: Literatur: P. E. Schurr et al., *Atherosclerosis Drug Discovery* (1976), published by C. E. Day; Plenum, New York, page 215.

Young male rats with an average body weight of 100 gm were made hypercholesterolemic by feeding them for 4 days on a diet consisting of 10% coconut oil, 1.5% cholesterol, 0.5% cholic acid, 0.2% choline chloride and 15% sucrose. While continuing with the diet, the test compound was administered in a methyl cellulose suspension by esophageal tube on two successive days. The animals were then made to fast overnight and 24 hours after the final administration of the test compound a blood sample was taken in order to obtain serum.

In the serum, the total cholesterol was determined enzymatically (Boehringer Mannheim Test Combination 126 039) and the β-lipoproteins were determined by nephelometry, after precipitation with $Ca^{++}$ and heparin, in the Autoanalyzer. The percentage reduction was calculated by comparison with a control group:

TABLE I

| | | Percentage reduction compared with controls | |
|---|---|---|---|
| Compound | Dose mgm/kg | Cholesterol in the serum | β-lipoproteins in the serum |
| B | 50 | −21 | −51 |

(b) Test on the normolipemic rat:
Male normolipemic rats with an average body weights of 250 to 300 gm were given the test compound by esophageal tube twice with an interval of 20 hours.

At the start of the test, the animals were deprived of food but had free access to drinking water. The serum cholesterol levels were determined enzymatically (Boehringer Mannheim Test Combination 126.039) after 28 and 44 hours. The percentage reduction was calculated in comparison with a control group:

TABLE II

| Compound | Dose mg/kg | Percentage reduction compared with control Total cholesterol in the serum |
|---|---|---|
| A | 1.1 | −26 |
| B | 20.0 | −20 |

2. Antithrombotic Activity:

(a) The thrombocytes of healthy human test subjects were incubated for 10 minutes at 37° C. with the test substance (final concentration: $1 \times 10^{-4}$ mol/l). Then, aggregation was initiated with collagen in the Born test in the usual way. Shortly before aggregation was initiated, a small quantity of supernatant liquid containing prostacycline, which was obtained from rings of aorta placed in the TRIS buffer, was added to the test sample. The quantity of supernatant liquid containing prostacycline was selected so that on its own it had little or no inhibiting effect. The sample incubated with the substance reacted with $PGI_2$ to give an inhibition of aggregation which was more than additive. This is shown in the following table:

TABLE III

| | n | mm height of curve (Born test) | % inhibition of thrombocyte aggregation |
|---|---|---|---|
| Control | 4 | 129 | |
| PRP* + compound C | 4 | 101 | 20.7 |
| PRP + $PGI_2$ | 4 | 90 | 30 |
| PRP + compound C + $PGI_2$ | 4 | 38 | 69 |

*PRP = platelet-rich plasma
n = number of tests (b) Demonstration of adenosine-potentiating effect in the Born Test.

The same procedure was used as in paragraph 2(a). The quantity of adenosine was selected so that, on its own, it produced only a slight inhibiting effect. The following table shows that the test compound, together with adenosine, produces an inhibiting effect which is more than additive.

TABLE IV

| | n | mm height of curve (Born test) | % inhibition of thrombocyte aggregation |
|---|---|---|---|
| Control | 4 | 114 | |
| PRP+ + compound C ($1 \times 10^{-4}$) | 4 | 75 | 33 |
| PRP+ + adenosine | 4 | 91 | 20 |
| PRP+ + compound C + adensine | 4 | 44 | 61 |

+PRP = platelet-rich plasma
n = number of tests (c) Prostacycline-reinforcing effect after oral administration in animals:

Rats weighing 450 gm were given the compound orally at a dose of 20 mg/kg; then, after one hour, a blood sample was taken and the Born Test was carried out as described above. The following table shows that, here again, a more than additive effect in conjunction with $PGI_2$, corresponding to the tests in vitro, is obtained (averages from three sets of tests on four animals):

TABLE V

| Animals treated with 20 mg/kg per os of compound C | 4% inhibition of aggregation |
|---|---|
| Plasma of control animals + $PGI_2$ | 20% inhibition of aggregation |
| Animals treated with compound C + $PGI_2$ | 100% inhibition of aggregation |

3. Acute toxicity

Compounds A, B and C are virtually non-toxic, since no toxic side effects were observed even at the maximum doses used (50 mg/kg per os).

In view of their pharmacological properties, the compounds of the present invention are useful for the treatment of hyperlipemia, particularly types IIA, IIB and IV, and resultant atherosclerotic changes in the vascular system, for the prophylaxis of thromboembolic diseases such as coronary infarct, cerebral infarct, transient ischaemic attacks, amaurosis fugax and for the prophylaxis of arteriosclerosis and metastatis formation.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like.

The daily dose for the treatment of hyperlepemia is 0.14 to 2.85 mgm/kg, preferably 0.21 to 2.14 mgm/kg, and for the treatment of thromboembolic diseases and the prophylaxis of ateriosclerosis and metastasis it is 7.14 to 14.28 mgm/kg, preferably 8.57 to 12.85 mgm/kg, administered in 2 to 4 single doses.

The following examples illustrate a few pharmaceutical dosage unit compositions comprising a compound of the present invention as an active ingredient and represent the best modes contemplated of using the invention. The parts are parts by weight unless otherwise specified.

Example 39

Suppositories

The suppository composition is compounded from the following ingredients:

| | |
|---|---|
| 6-Benzyl-5,6,7,8-tetrahydro-4H—thieno[2,3-d]azepine-2-carboxylic acid hydrochloride | 30 parts |
| Suppository base (e.g. cocoa butter) | 1,670 parts |
| Total | 1,700 parts |

Preparation

The pulverized active ingredient is homogeneously blended into the suppository base which had previously melted and cooled to 40° C. 1700 mgm portions of the composition are poured into cooled suppository molds and allowed to harden therein. Each suppository is a rectal dosage unit composition containing 30 mgm of the active ingredient.

Example 40

Gelatin Capsules

The capsule filler composition is compounded from the following ingredients:

| | |
|---|---|
| 6-Benzyl-5,6,7,8-tetrahydro-4H—thieno[2,3-d]azepine-2-carboxylic acid hydrochloride | 5.0 parts |
| Dried corn starch | 100.0 parts |
| Powdered corn starch | 93.0 parts |
| Magnesium stearate | 2.0 parts |
| Total | 200.0 parts |

Preparation

The ingredients are admixed with each other, the mixture is passed through a 0.75 mm-mesh screen and then homogenized in a mixer, and 200 mgm portions of the resulting powdery composition are filled into No. 3 hard gelatin capsules. Each capsule is an oral dosage unit composition containing 5 mgm of the active ingredient.

Example 41

Tablets

The table composition is compounded from the following ingredients:

| | |
|---|---|
| 6-(2-Chloro-benzyl)-5,6,7,8-tetrahydro-4H—thieno[2,3-d]-azepine hydrochoride | 300 parts |
| Lactose | 120 parts |
| Microcrystalline cellulose | 100 parts |
| Corn starch | 72 parts |
| Polyvinylpyrrolidone | 6 parts |
| Magnesium stearate | 2 parts |
| Total | 600 parts |

Preparation

The active ingredient, the lactose, the cellulose and the corn starch are intimately admixed with each other, the mixture is uniformly moistened with an aqueous 15% solution of the polyvinylpyrrolidone, the moist mass is passed through a 1.5 mm-mesh screen, and the resulting granulate is dried at 45° C. on a drying rack. The dry granulate is again passed through the screen and then admixed with the magnesium stearate, and the composition is compressed into 600 mgm-tablets. Each tablet is an oral dosage unit containing 300 mgm of the active ingredient.

Example 42

Coated Pills

The pill core composition is compounded from the following ingredients:

| | |
|---|---|
| 6-(2-Chloro-benzyl)-5,6,7,8-tetrahydro-4H—thieno[2,3-d]-azepine hydrochloride | 250 parts |
| Lactose | 100 parts |
| Microcrystalline cellulose | 40 parts |
| Corn starch | 84 parts |
| Polyvinylpyrrolidine | 5 parts |
| Magnesium stearate | 1 parts |
| Total | 480 parts |

Preparation

The ingredients are compounded in the same manner as in Example 41, and the composition is compressed into 480 mgm-pill cores which are subsequently coated with a thin shell consisting essentially of sugar and polished beeswax. Each coated pill is an oral dosage unit composition containing 250 mgm of the active ingredient.

Any one of the other compounds embraced by formula I or a non-toxic, pharmacologically acceptable salt thereof may be substituted for the particular active ingredient in Examples 39 through 42. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

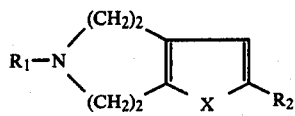

wherein
X is oxygen, sulfur, imino, methylimino, phenylimino or benzylimino;
$R_1$ is alkyl of 1 to 3 carbon atoms; unsubstituted mono- or di-substituted benzyl, where the substituents are chlorine or bromine; chloro-hydroxybenzyl; bromo-hydroxybenzyl; unsubstituted or mono-substituted benzoyl, where the substituent is chlorine or bromine; alkoxycarbonyl of 2 to 4 carbon atoms; allyl; dodecyl, chloromethoxybenzoyl; or benzyloxycarbonyl; and
$R_2$ is hydrogen, alkoxycarbonyl of 2 to 4 carbon atoms or carboxyl;
a non-toxic, pharmacologically acceptable acid addition salt thereof; or, when $R_2$ is carboxyl, a non-toxic, pharmacologically acceptable salt thereof formed with an inorganic or organic base.

2. A compound of claim 1, where
X is sulfur;
$R_1$ is dodecyl, benzyl, chlorobenzyl or chlorobenzoyl; and
$R_2$ is hydrogen or carboxyl,
a non-toxic, pharmacologically acceptable acid addition salt thereof; or, when $R_2$ is carboxyl, a non-toxic, pharmacologically acceptable salt thereof formed with an inorganic or organic base.

3. The compound of claim 1 which is 6-(2-chlorobenzoyl)-5,6,7,8-tetrahydro-4H-thieno[2,3-d]azepine.

4. A compound of claim 1, which is 6-(2-chlorobenzoyl)-5,6,7,8-tetrahydro-4H-thieno[2,3-d]azepine or a non-toxic, pharmacologically acceptable acid addition salt thereof.

5. A compound of claim 1, which is 6-benzyl-5,6,7,8-tetrahydro-4H-thieno[2,3-d]azepine-2-carboxylic acid or a non-toxic, pharmacologically acceptable salt thereof.

6. An antithrombotic pharmaceutical composition consisting essentially of an inert pharmaceutical carrier and an effective antithrombotic amount of a compound of claim 1.

7. The method of preventing or relieving thrombosis in a warm-blooded animal, which comprises perorally, parenterally or rectally administering to said animal an effective antithrombotic amount of a compound of claim 1.

* * * * *

UNITED STATES PATENT AND TRADEMARK OFFICE
CERTIFICATE OF CORRECTION

PATENT NO. : 4,414,225
DATED : November 8, 1983
INVENTOR(S) : ROBERT SAUTER ET AL.

It is certified that error appears in the above-identified patent and that said Letters Patent is hereby corrected as shown below:

Title page, [57] line 14 of Abstract after structural formula; and Column 1, line 41: "phenyl)e-" should read -- phenyl)- --.

Title page, [57] line 15 of Abstract after structural formula; and Column 1, line 42: "thylaminocarbonyl" should read -- ethylaminocarbonyl --.

Column 2, line 2: "phenylethox-" should read -- phenylethoxy- --
Column 2, lines 3 and 7: "ycarbonyl" should read -- carbonyl --.
Column 2, line 6: "propox-" should read -- propoxy- --.
Column 11, lines 27-28: "500 ml" should read -- 50 ml --.
Column 13, line 67: "N-4.96%" should read -- N-4.86% --.
Column 17, line 18: "H-5.78%" should read -- H-5.87% --.
Column 18, line 16: Delete "L %;".
Column 18, line 21: "2amino-" should read -- 2-amino- --.
Column 21, line 19: "Melding" should read -- Melting --.
Column 21, line 25: "[2,3-]" should read -- [2,3-d] --.
Column 25, line 28: "[2,3]" should read -- [2,3-d] --.
Column 25, line 45: "1.53 g" should read -- 1.54 g --.
Column 26, line 1: "methylamin-" should read -- methylamino- --.
Column 26, line 2: "oacetate" should read -- acetate --.

UNITED STATES PATENT AND TRADEMARK OFFICE
CERTIFICATE OF CORRECTION

PATENT NO. : 4,414,225

DATED : November 8, 1983

INVENTOR(S) : ROBERT SAUTER ET AL.

It is certified that error appears in the above-identified patent and that said Letters Patent is hereby corrected as shown below:

Column 26, line 21: Delete "e".
Column 26, line 22: "thanol" should read -- ethanol --.
Column 29, line 59: "[2,3-azepine" should read
-- [2,3-d]azepine --.

Signed and Sealed this

Sixth Day of March 1984

[SEAL]

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,414,225
DATED : November 8, 1983
INVENTOR(S) : ROBERT SAUTER ET AL.

It is certified that error appears in the above-identified patent and that said Letters Patent is hereby corrected as shown below:

Column 34, lines 1 and 2 of Claim 4:

"6-(2-chlorobenzoyl)" should read

-- 6-(2-chlorobenzyl) --.

Signed and Sealed this

Fifteenth Day of May 1984

[SEAL]

Attest:

GERALD J. MOSSINGHOFF

Attesting Officer

Commissioner of Patents and Trademarks